(12) United States Patent
Pawluczyk et al.

(10) Patent No.: US 9,599,507 B2
(45) Date of Patent: Mar. 21, 2017

(54) FIBER OPTIC PROBE FOR REMOTE SPECTROSCOPY

(71) Applicants: Rafal Pawluczyk, Kitchener (CA); Paul Fournier, Kitchener (CA)

(72) Inventors: Rafal Pawluczyk, Kitchener (CA); Paul Fournier, Kitchener (CA)

(*) Notice: Subject to any disclaimer, the term of this patent is extended or adjusted under 35 U.S.C. 154(b) by 0 days.

(21) Appl. No.: 14/766,068

(22) PCT Filed: Feb. 5, 2014

(86) PCT No.: PCT/CA2014/050071
§ 371 (c)(1),
(2) Date: Aug. 5, 2015

(87) PCT Pub. No.: WO2014/121389
PCT Pub. Date: Aug. 14, 2014

(65) Prior Publication Data
US 2015/0377701 A1    Dec. 31, 2015

Related U.S. Application Data

(60) Provisional application No. 61/761,021, filed on Feb. 5, 2013.

(51) Int. Cl.
*G01J 3/00* (2006.01)
*G01J 3/44* (2006.01)
(Continued)

(52) U.S. Cl.
CPC ............. *G01J 3/0218* (2013.01); *G01J 3/021* (2013.01); *G01J 3/0208* (2013.01);
(Continued)

(58) Field of Classification Search
CPC ........ G01J 3/0208; G01J 3/021; G01J 3/0218; G01J 3/0221; G01J 3/0243; G01J 3/2823;
(Continued)

(56) References Cited

U.S. PATENT DOCUMENTS

| 4,573,761 A | 3/1986 | McLachlan et al. |
| 5,112,127 A | 5/1992 | Carrabba et al. |

(Continued)

OTHER PUBLICATIONS

T. F. Cooney, et al., "Comparative Study of Some Fiber-Optic Remote Raman Probe Designs. Part I: Model for Liquids and Transparent Solids", *Applied Spectroscopy*, vol. 50 (7), pp. 836-848 (1996).

(Continued)

*Primary Examiner* — Sunghee Y Gray
(74) *Attorney, Agent, or Firm* — Heslin Rothenberg Farley and Mesiti, PC

(57) ABSTRACT

A fiber optic probe assembly is provided. The probe comprises a first optical system and a second optical system, a delivery light guide comprising one or more than one delivery optical fiber for transmitting excitation radiation from a radiation source disposed at a proximal end of the light guide to the first optical system. The first optical system comprising one or more than one first optical element for forming a substantially collimated illumination beam from the excitation radiation. An optically opaque tubular sleeve is fitted over the first optical system to optically isolate the first optical system and the delivery light guide from the second optical system. The second optical system comprising one or more than one second optical element for gathering optical radiation scattered from a sample and forming the optical radiation into a collection beam. A collection light guide comprising one or more than one collection optical fiber receives the collection beam and transmits the collection beam to an analyzer. The first and second optical systems are disposed within a housing so that an emission cone of the first optical system and an acceptance cone of the second optical system substantially overlap. A spectroscopic measurement system comprising the optic fiber probe is also provided.

16 Claims, 13 Drawing Sheets

(51) Int. Cl.
*G01J 3/02* (2006.01)
*G01N 21/65* (2006.01)
*G01J 3/28* (2006.01)
*G01N 21/47* (2006.01)

(52) U.S. Cl.
CPC .......... *G01J 3/0221* (2013.01); *G01J 3/0243* (2013.01); *G01J 3/2823* (2013.01); *G01J 3/44* (2013.01); *G01J 3/4412* (2013.01); *G01N 21/65* (2013.01); *G01N 2021/4742* (2013.01); *G01N 2021/656* (2013.01)

(58) Field of Classification Search
CPC .. G01J 3/44; G01J 3/4412; G01N 2021/4742; G01N 2021/656; G01N 21/65
USPC .................................................. 356/300, 301
See application file for complete search history.

(56) References Cited

U.S. PATENT DOCUMENTS

| | | |
|---|---|---|
| 5,377,004 A | 12/1994 | Owen et al. |
| 5,420,508 A | 5/1995 | Smith |
| 5,615,673 A | 4/1997 | Berger et al. |
| 5,953,477 A | 9/1999 | Wach et al. |
| 6,038,363 A | 3/2000 | Slater et al. |
| 6,411,838 B1 | 6/2002 | Nordstrom et al. |
| 7,647,092 B2 | 1/2010 | Motz et al. |
| 2008/0030728 A1* | 2/2008 | Nguyen ............... G01J 3/02 356/328 |
| 2012/0127467 A1* | 5/2012 | Ivanov ............... G01N 21/6408 356/326 |

OTHER PUBLICATIONS

T. F. Cooney, et al., "Comparative Study of Some Fiber-Optic Remote Raman Probe Designs. Part II: Tests of Single Fiber, Lensed, and Flat- and Bevel-Tip Multi-Fiber Probes", *Applied Spectroscopy*, vol. 50 (7), pp. 849-860 (1996).

I. R. Lewis, et al., "Raman Spectrometry with Fiber-Optic Sampling", *Applied Spectroscopy*, vol. 50 (10), pp. 12A-30A (1996).

U. Utzinger et al., "Fiber Optic Probes for Biomedical Optical Spectroscopy", *Journal of Biomedical Optics*, vol. 8(1), pp. 121-147 (2003).

International Search Report for PCT/CA2014/050071.

* cited by examiner

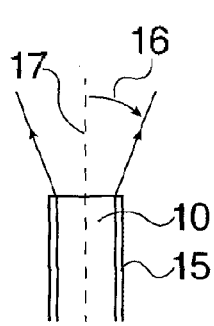
FIG. 5A
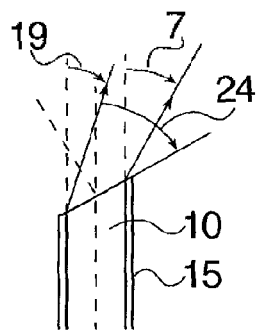
FIG. 5B
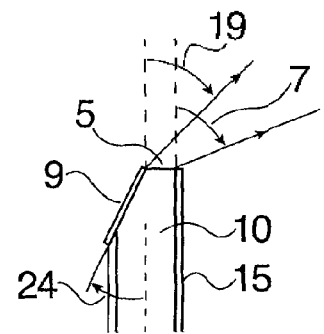
FIG. 5C
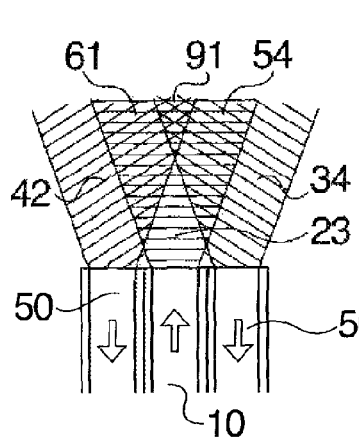
FIG. 5D
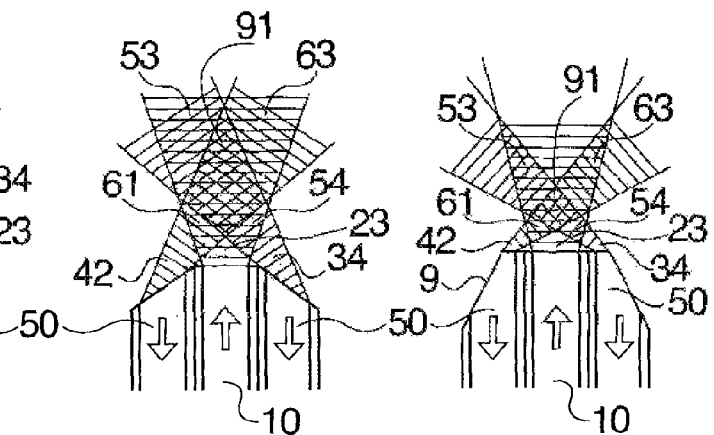
FIG. 5E
FIG. 5F

FIBER OPTIC PROBE FOR REMOTE SPECTROSCOPY

CROSS-REFERENCE TO RELATED APPLICATIONS

This application is the U.S. National Filing of PCT Application No. PCT/CA2014/050071 filed on Feb. 5, 2014 and published in English as WO 2014/121389 A1 on Aug. 14, 2014, and claims the priority of U.S. provisional application Ser. No. 61/761,021 filed Feb. 5, 2013, the entire contents of these applications are hereby incorporated by reference.

FIELD OF INVENTION

The present invention relates to a fiber optic probe. The fiber optic probe may be lensed and filtered and comprise two coaxial but optically isolated and independent beam paths.

BACKGROUND OF THE INVENTION

Quick and reliable chemical analysis of substances is a critical requirement in many industries. Many currently available analytical techniques involve an interaction of optical radiation with the sampled substance, where the molecules of the sample absorb at least some of the energy from the incident radiation. This energy can then be re-emitted through: diffuse reflectance (strong signal at the same wavelength, almost instantaneous); Raman scattering (very weak signal at a slightly shifted wavelength, almost instantaneous); and fluorescence (weak signal at a longer wavelength, time delayed, decaying with time).

Raman spectroscopy, in particular, is suitable for chemical analysis and monitoring. Raman frequency shifts are specific to the molecular vibrations. The presence of particular peaks in a Raman spectrum is indicative of particular molecular bonds and thus "fingerprints" a particular molecule. The intensities of Raman peaks are proportional to the chemical concentration of that molecule. Thus, Raman spectroscopy can be used to determine the sample composition both qualitatively, and, with proper calibration, quantitatively.

Many applications of chemical analysis involve aqueous samples. Raman spectroscopy is suitable for these applications, as water has very low absorption in the spectral region where most Raman shifts occur. Raman spectroscopy also does not require any particular sample preparation and can be used non-invasively (for example, through a vial). This makes it ideal for measurements in biomedical, environmental and process control applications, especially when combined with fiber optic sampling.

Optical fibers, including those based on fused silica glass, are useful for conducting spectroscopic measurements. Optical fibers transmit optical radiation efficiently over significant distances and enable remote measurements, for example, in hazardous environments by decoupling the measuring instrument from the sample to be measured. The design parameters of the optical fibers such as core diameter, numerical aperture and transmission range can be selected to best match the characteristics of both the sample and the instrument in use. Due to the size and flexibility of the optical fibers, measurements of small samples in confined spaces (such as in environmental monitoring, in-line process control or in-vivo biomedical applications) are possible.

Optical fibers can be packaged with additional components such as lenses, filters, mirrors into application specific fiber optic probes.

In a typical Raman spectroscopy system comprising of spectrograph, fore optics, fiber bundles and remote fiber probe, it is usually either the spectrograph or the fiber bundle that determines the overall throughput (or "étendue"). As a result there is no advantage to collecting light which will not be later captured by the spectrograph. However, the design of the remote probe can be optimized to best match the capabilities of the spectrograph and the bundle.

Therefore, it is relevant to consider, amongst others, several factors in the design of fiber optic probes for remote spectroscopy: efficient collection of the back-scattered radiation (throughput); efficient rejection of the excitation radiation; the necessity to deal with spurious signals such as Rayleigh scattering and silica Raman coming from the fiber itself which often swamps the useful collected signal; and optimal coupling from the probe into the other parts of the system.

Fiber optic Raman designs in which one optical fiber delivered the excitation radiation to the sample and one or more collection fibers guided the collected signal to the analytical instrument are known. The collection fibers are arranged in parallel in one or more concentric rings surrounding the excitation fiber, resulting in low overlap between their respective emission and collection cones, with a zone of zero overlap close to the excitation fiber where the excitation radiation is the most intense. U.S. Pat. No. 4,573,761 (McLachlan) describes a design that decreases the zero overlap zone by tilting the fibers at the probe tip. U.S. Pat. No. 5,420,508 (O'Rourke) describes angle polishing, in order to improve the overlap and decreasing the zero overlap zone.

While compact and robust, these designs have several shortcomings. Since the excitation beam expands upon exiting the delivery fiber, the measurement area on the sample is fairly large, while the excitation radiation density is low. As a result the useful depth of focus of the probe is limited. Additionally, the collection fibers pick up the (useful) Raman signal, and also Rayleigh scattered excitation radiation which usually overwhelms the Raman signal. Furthermore, the interaction of the excitation radiation with fused silica generates a silica Raman signal which accumulates over the length of the fiber. For probes several meters in length, silica Raman became a major component of collected spectral data. These problems can be mitigated to some degree by using additional optical components in the probe to manipulate and filter both excitation and collection beams, thus improving the quality of collected signal. Generally, probes incorporating such additional optical components work by imaging the excitation fiber face to a spot on the sample and then re-imaging that spot onto the collection fibers, and are thus called imaging probes.

It is advantageous to perform filtering as close to the sample as possible. A conventional approach is to use a narrow laser band pass component close to the end of the excitation beam path and a rejection component placed between the sample and the collection beam path. The laser band pass ensures that only single frequency laser radiation is delivered to the sample, while the silica Raman signal as well as the Rayleigh scattered light from the fiber are either reflected back into the fiber or out of the system. After the interaction of the excitation radiation with the sample, the back-scattered signal contains both unshifted Rayleigh scattered excitation light and shifted Raman signal. The Rayleigh signal is much stronger (usually by several orders of magnitude) and should be prevented from entering the collection beam path. This can be accomplished with several types of components such as notch or long pass filters.

Several prior art designs are discussed in the following review articles'. F. Cooney, et. el., *Appl. Specrosc.* 50 (7), 836-848 (1996); T. F. Cooney, *Appl. Spectrosc.* 50 (7), 849-860 (1996); I. R. Lewis, and P. R. Griffiths, *Appl. Spectrosc.* 50 (10), 12A-30A (1996); and U. Utzinger, and R. R. Richards-Kortum, *J. Biomed. Opt.* 8, 121-147 (2003).

U.S. Pat. No. 5,112,127 (Carraba, et al.; see FIG. 1) teaches a design which incorporates optical components (a bandpass filter to clean up the excitation radiation, a dichroic filter to combine the two beam paths and a long pass filter to filter out silica Raman from collected signal) to selectively remove unwanted scattering from the collected signal. This design requires a very high performance dichroic filter which transmits a narrow band of excitation radiation to the sample and reflects a wide band of wavelengths into the collection path efficiently. Such components are difficult to manufacture and their performance varies with wavelength, affecting the relative strength of the Raman peaks observed. The physical layout of the probe makes it also fairly bulky, acceptable for industrial and lab use, but not practical for biomedical in-vivo work.

U.S. Pat. No. 5,377,004 (Owen et al.; FIG. 2) teach of a probe design with a collection beam path in-line with the sample, and with an excitation path folded into the main probe axis from the side. The beam combining element needs to be highly reflective over a narrow band and transmissive elsewhere. The probe employs holographic optical elements to filter and combine beams.

U.S. Pat. No. 5,615,673 (Berger, et al.) teaches a design capable of being used for biomedical applications where very low signals are observed. In order to improve collection efficiency, an additional parabolic component is placed in front of the probe which converts the collected radiation from a highly angular to almost parallel beam compatible with collection fiber acceptance angle. The tradeoff is that the collection bundle becomes larger and requires additional reformatting at the instrument input.

U.S. Pat. No. 5,953,477 (Wach, et al.) teaches of many techniques that can be applied to fiber optic Raman probes. In particular, it discloses a probe design in which the collection fibers are partially ground and coated with reflective layers in order to shape their collection cones away from the fiber axis and thus to improve the overlap between the excitation and collection volumes (while at the same time almost eliminating the dead space of zero overlap), resulting in a fivefold improvement in signal intensity over a beveled face probe design. The probe also incorporates small filtering elements coated directly onto the fibers to provide some of the advantages of filtered probes in a compact package. However, it is difficult to fabricate high performance filters on optical fiber faces with current technology. In addition, such filters perform sub-optimally as they are placed in converging light beams. Thus, these probes could not match the performance of imaging probes.

U.S. Pat. No. 6,038,363 (Slater, et al.; FIG. 3) discloses a probe with reduced background luminescence. This is achieved by introducing a transmissive combiner placed in the collection beam, with a small reflective aperture in the center which folded in the excitation beam into the probe optical path. Unlike the previous imaging probe designs, the beam combining is done not in amplitude (by filtering parts of the light away in expanded beams) but by wavefront (by blocking part of the probe aperture).

U.S. Pat. No. 7,647,092 (Motz, et al.; FIG. 4) discloses a non-imaging probe design with integral filtering, comprising a doughnut shaped long pass filter for collection, and a very small round band pass filter for excitation filtering. Beam steering is accomplished by adding a ball lens at the probe tip. The whole probe is under 2 mm in diameter and compatible for use with endoscopic medical applications.

In imaging probes described above, the overlapped excitation and collection beams are focused onto the sample using a common final lens element. This arrangement requires that the two beams are focused at the same distance from the probe, resulting in optimal overlap between excitation and collection volumes.

The overall throughput of these probes is often limited by either light gathering capability (characterized by the relative aperture, or f-number F/#) of the spectrograph used or by acceptance angle of the collection fibers (characterized by the numerical aperture, NA). In principle, for efficient coupling into the spectrograph, the acceptance cone of a collection fiber should be matched to the acceptance cone of the spectrograph. This has implications for the design of the probe itself, as the relative aperture of the collection optics should be matched to the fibers. The fastest commercial spectrographs have F/# of 1.8. Optical fibers with matching NA of 0.28 are available, but less common than the 0.22 NA fibers (equivalent to F/# of 2). Constructing an imaging system with such low F/# requires multi-lens assemblies. So, in conventional designs there is a trade-off between the volume illuminated by the excitation channel, the solid angle from which the same optics can collect the back-scattered signal and coupling that collected light into the spectrograph In conventional imaging probe designs, the excitation and collection paths are routed in separate fibers, and the excitation and collection beams are expanded and overlapped within the probe body. To achieve their overlap, beam-combining components are employed, such as a dichroic filter, a narrow bandpass filter, a diffraction grating or a partial aperture mirror. Some loss of collected signal occurs in all the probe designs discussed above. Also, since the optical paths are overlapped, the excitation radiation is scattered back into the probe, increasing its background level.

An approach in which the two optical paths are isolated and independent is disclosed in U.S. Pat. Nos. 6,411,838 and 6,760,613 (Nordstrom et al.). This system uses a substantially coaxial and confocal configuration of emission and collection optical systems which are optically isolated. The illumination and detection systems are coaxial and arranged so that the excitation system forms a central obscuration within the illumination system, resulting in a central spot with no signal at the image plane of the illumination system.

SUMMARY OF THE INVENTION

The present invention relates to a fiber optic probe. The fiber optic probe may be lensed and filtered and comprise two coaxial but optically isolated and independent beam paths. The fiber optic probe may be used in remote spectroscopy.

It is an object of the invention to provide an improved fiber optic probe.

According to the present invention there is provided a fiber optic probe assembly comprising, a housing for containing a first optical system and a second optical system, a delivery light guide comprising one or more than one delivery optical fiber for transmitting excitation radiation from a radiation source disposed at a proximal end of the light guide to the first optical system, the first optical system comprising one or more than one first optical element, the one or more than one first optical element for forming a substantially collimated illumination beam from the excitation radiation, an optically opaque tubular sleeve fitted over the first optical system to optically isolate the first optical system and the delivery light guide from the second optical system so that the excitation radiation transmitted by the delivery light guide exits through an exit face of the first optical system, the second optical system comprising one or more than one second optical element for gathering optical radiation scattered from a sample and forming the optical radiation into a collection beam, a collection light guide comprising one or more than one collection optical fiber for accepting the collection beam and transmitting the collection beam to an analyzer, the first and second optical systems are disposed within the housing so that an emission cone of the first optical system and an acceptance cone of the second optical system substantially overlap.

The disclosure also provides the fiber optic probe described above wherein the one or more than one second optical element comprises a collimating optical element for collimating the collection beam to produce a collimated beam and a focusing optical element, for focusing collimated beam into the collection light guide. The one or more second optical element may further comprise one or more than one filter element positioned between the collimating optical element and the focusing optical element.

The present invention provides the fiber optic probe described above, wherein the one or more than one first optical element comprises a collimating optical element for collimating the excitation radiation to produce the collimated illumination beam and a focusing optical element, for focusing the collimated illumination beam. The one or more first optical element may further comprise one or more than one filter element positioned between the collimating optical element and the focusing optical element. Furthermore, the one or more than one first optic element of the first optical system may be selected from a refractive optical lens, and a gradient index optical lens.

The fiber optic probe as described above may further comprising an optically transparent window element disposed at a sample face of the second optical system, the window element receives the optical radiation scattered by the sample, and isolates the fiber optic probe from the sample.

The fiber optic probe described above, wherein the delivery light guide, the collection light guide, or both the delivery light guide and the collection light guide is comprised of a multi mode optical fiber. The collection light guide may also be comprised of a plurality of multi mode optical fibers disposed in a parallel bundle. The fiber optic probe may also comprise a rigid termination at a proximal end of the collection light guide, whereby individual optical fibers of the collection light guide are disposed in a side by side linear array for coupling into an analysis device.

The present invention also provides an spectroscopic measurement system comprising, a fiber optic probe assembly comprising, a housing for containing a first optical system and a second optical system, a delivery light guide comprising one or more than one delivery optical fiber for transmitting excitation radiation from a radiation source disposed at a proximal end of the light guide to the first optical system, the first optical system comprising one or more than one first optical element, the one or more than one first optical element for forming a substantially collimated illumination beam from the excitation radiation, an optically opaque tubular sleeve fitted over the first optical system to optically isolate the first optical system and the delivery light guide from the second optical system so that the excitation radiation transmitted by the delivery light guide exits through an exit face of the first optical system, the second optical system comprising one or more than one second optical element for gathering optical radiation scattered from a sample and forming the optical radiation into a collection beam, a collection light guide comprising one or more than one collection optical fiber for accepting the collection beam and transmitting the collection beam to an analyzer;

the radiation source in optical communication with a proximal end of the delivery light guide, the analyzer comprising a spectrograph with an entrance aperture and a radiation detector, the entrance aperture disposed in an object plane of the spectrograph and coupled to the proximal end of the collection light guide, the radiation detector disposed in an image plane of the spectrograph.

The entrance aperture of the spectroscopic measurement system described above may be rectangular and elongated in one dimension. Furthermore, the collection light guide may be comprised of a plurality of like optical fibers, disposed in a closely hexagonally packed circular bundle at a distal end of the collection light guide, and in a closely packed linear array at the proximal end of the collection light guide. The spectroscopic measurement system of may further be characterized with a low input numerical aperture of the second optical system, to produce an overlap of an illumination volume produced by the collimated illumination beam of the first optical system, and a collection volume of the second optical system, suitable for measurements from weakly scattering samples.

The spectroscopic measurement system described above may further comprise an optically transparent window positioned at a sample face of the fiber optic probe body The present disclosure relates to fiber optic probes where excitation and collection channels are completely optically isolated to decrease stray light, and filtering components are placed in collimated beam paths for optimal performance. The fiber optic probe comprise two optically isolated, independent optical systems that are arranged coaxially: 1) an excitation system to deliver excitation radiation, for example, laser radiation to the sample, and 2) a collection system to couple the scattered radiation after interaction with a sample, for example Raman signals, into a collection bundle.

The focal length, spot size and depth of focus can be set independently for both the excitation and collection systems, overall probe throughput and efficiency are optimized Excitation and collection beams are overlapped outside of the probe body itself, and the degree of overlap can be controlled on an application by application basis by selecting appropriate optical components.

The present disclosure also relates to "étendue management" by decoupling collection and excitation optical systems. "Étendue" describes the fundamental radiation gathering capability of an optical system as product of the solid angle under which the object observed is visible at the entrance pupil and of the pupil area. It is the limiting factor of the system throughput. In systems where radiation is limited, great care is usually taken to preserve étendue. As most optical systems consist of several parts, overall system performance is limited by the part with the highest étendue. The collection system can be considered as one series of modules (probe optics, fiber bundle, coupling optics, spectrograph, detector, etc) and the excitation system as another series (radiation source, coupling optics, delivery fiber, probe optics, etc). The present disclosure relates to independent optimization of both of these systems.

Raman scattering in most samples is a directionless process (Raman shifted radiation is scattered in all directions equally), therefore, throughput of radiation within a probe depends mainly on a spot size on the sample, and the acceptance angle. In general, the throughput of the entire spectroscopic system is limited by the collection system. In some situations, it may be advantageous to have an almost collimated excitation beam to increase the volume in which excitation radiation interacts with the sample, and to be able to collect radiation from a larger solid angle. The fiber optic probe of the present disclosure makes this possible, for example, using an F/8 lens to slowly focus the excitation beam, and a faster F/2 lens of larger diameter to collect the signal from a larger volume. For other types of samples, it may be advantageous to have the excitation radiation tightly focused to small spot, yet still be able to collect light from a large solid angle. This configuration is also possible with the present disclosure.

In the present disclosure, two beam paths are decoupled and independent from each other. For example, the two channels may be concentric and parallel to each other, with an excitation channel exiting through an aperture in the front component of a collection channel. With this configuration, the collection lens system is thus partially obscured (central obscuration).

Because this obscuration occurs in a pupil space, the obscuration is not visible at an image plane of the collection system (located at the collection bundle end face). The central obscuration blocks the Rayleigh scattered excitation radiation from entering the collection path. This serves to lower overall probe background and is useful for highly reflective samples. The central obscuration acts as a baffle and creates a dead zone in front of the probe where there is no overlap between the excitation and collection beams. An object placed within this zone, such as a protective window at the probe tip, or wall of a cuvette will be invisible to the probe. Even if a Raman signal is generated by this object upon exposure to the excitation radiation, it will not be collected by the probe. This enables measurements inside containers, for example, or depth sampling inside solid objects such as interior of a pill through its coating.

While the central obscuration reduces the collected signal, a fraction of signal blocked by the obscuration decreases rapidly as a ratio of the collection to excitation channel diameters increases.

The overlap zone where the excitation and collection beams overlap, starts only at a certain distance from a last lens element. In situations where fast collection optics (F/# below 2) are employed, the overlap zone starts close to a focal plane of both optical systems (the excitation and collection systems) and may be shallow—its depth may be comparable to the spot size itself. This allows for "quasi-confocal" use of the probe, where signal is detectable only from a thin layer of the sample.

Since the collection optical system of the present disclosure is an imaging system, it will create an image of the spot the probe is focused onto, at the input face of the collection fiber bundle. Raman scattered radiation from a certain region of the sample will be focused at a particular patch of the collecting optics image plane, and thus into a particular fiber. Provided the fibers are of small enough size and that their position within the collection bundle is correlated to their position in an entrance slit of an imaging spectrograph, a spectral map of the sample can be recreated.

As described herein, the excitation radiation is delivered to the probe by means of one or more, for example a single, optical fiber. This fiber is routed through a channel on an outside of the collection channel optical system, and is then folded into the center of the collection channel. In order to minimize the space required, and allow for sharp bends of the excitation fiber, the excitation fiber is housed in a small diameter optically opaque tube which is bent to the required shape. The tube serves several purposes: it holds the bent fiber in place, protects it from mechanical shocks and optically isolates it from the rest of the probe.

The isolation of the excitation beam path is accomplished, for example, by sheathing various sections in optically opaque materials throughout the body of the probe. The excitation fiber is routed inside an optically opaque small diameter tube up to an output end face. Light leakage from the excitation fiber is then further blocked by an additional optically opaque ferrule and larger optically opaque housing for the excitation path optical assembly. Optically opaque, light absorbing adhesives are used throughout the assembly.

The fiber optic probe described herein readily lends itself to miniaturization. For example, which is not to be construed as limiting in any manner, the probe may have an overall diameter below 4 mm and a rigid length of 30 mm. As would be understood by one of skill in the art, longer versions of such probes may be fabricated as required by adding an additional section of rigid tube over the excitation and collection fibers. Reduction in size of certain components may be used to achieve an overall probe diameter for example, but not limited to, below 2 mm or below 1 mm or below 0.5 mm, or any amount therebetween. At that size, the rigid section of the probe may be, for example which is not to be considered limiting, be less than 10 mm long or less than 5 mm long or less than 2 mm long, or any amount therebetween, thus enabling in-vivo endoscopic applications.

Another aspect of the present disclosure, leading to further improvement in throughput, is the arrangement of the collection fibers at the distal end of the probe into a linear array corresponding closely to the entrance slit of the spectrograph. This ensures that radiation from all collection fibers enters the spectrograph.

Additional fibers can be also added to linear array which can serve for reference or calibration purposes, for example to quantify the laser output or to ensure that proper wavelength calibration is achieved at all times.

Each of the delivery (first) and collection (second) optical systems of the fiber optic probe described herein comprise an optical element for collimating the collection beam to produce a collimated beam and a focusing optical element, for focusing the collimated beam. In the delivery optical system the focused collimated beam is directed onto a sample, while in the collection optical system, the collimated beam is focused into the collection light guide. The spacing between these optical elements may be adjusted to appropriately focus the beam as required (i.e. on the sample, and into the collection light guide). The first and second optical systems may also comprise a filter element positioned between the collimating optical element and the focusing optical element.

The lensed and filtered fiber optic probes as described herein are composed of two coaxial but optically isolated and independent beam paths. These probes offer improved control over light scattering spectroscopic measurements by separating the excitation and collection optical paths which can then be independently optimized for a given application.

The underlying principles described herein can be readily adapted to various modalities of remote spectroscopic measurements.

The fiber optic probes as described herein offer control over light scattering spectroscopic measurements by separating the excitation and collection optical paths which can then be independently optimized for a given application.

These, and other features of the fiber optic probe, including construction and combinations of components, will further described below. It is understood that particular apparatuses and systems embodying the fiber optic probe described herein are for the purpose of illustration only and are not to be considered limiting. The principles and features of the fiber optic probe may be employed in many varied embodiments without departing from the scope of the disclosure.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 4A shows a longitudinal section of the end of the probe. FIG. 4B shows a cross sectional view of the probe.

FIGS. 5A to 5F illustrates the effects of modifying the optical fibers to change their acceptance cones and the concept of overlap of excitation and collection cones (see specification for further details).

DETAILED DESCRIPTION

The present invention relates to a fiber optic probe. The fiber optic probe may be lensed and filtered and comprise two coaxial but optically isolated and independent beam paths.

The following description is of a preferred embodiment.

The headings provided are not meant to be limiting of the various embodiments of the invention. Terms such as "comprises", "comprising", "comprise", "includes", "including" and "include" are not meant to be limiting. In addition, the use of the singular includes the plural, and "or" means "and/or" unless otherwise stated. Unless otherwise defined herein, all technical and scientific terms used herein have the same meaning as commonly understood by one of ordinary skill in the art.

The present invention provides a fiber optic probe assembly comprising, a first optical system and a second optical system. The first and second optical systems are optically isolated and are comprised of separate optical components. The first optical system delivers excitation radiation to a sample surface and comprises a delivery light guide comprising one or more than one delivery optical fiber for transmitting excitation radiation from a radiation source disposed at a proximal end of the light guide to the first optical system. The light delivery guide is in optical communication with one or more than one first optical element that forms a substantially collimated illumination beam from the excitation radiation. An optically opaque tubular sleeve is fitted over the first optical system to optically isolate the first optical system and the delivery light guide from the second optical system, and permitting the excitation radiation transmitted by the delivery light guide to exit through an exit face of the first optical system and interact with a sample placed in the path of the collimated illumination beam. The second optical system comprises one or more than one second optical element for gathering optical radiation scattered from the sample and forming the optical radiation into a collection beam. The collection beam is transmitted through a collection light guide comprising one or more than one collection optical fiber to an analyzer. The first and second optical systems are disposed within a housing so that an emission cone of the first optical system and an acceptance cone of the second optical system substantially overlap.

Figure 1:
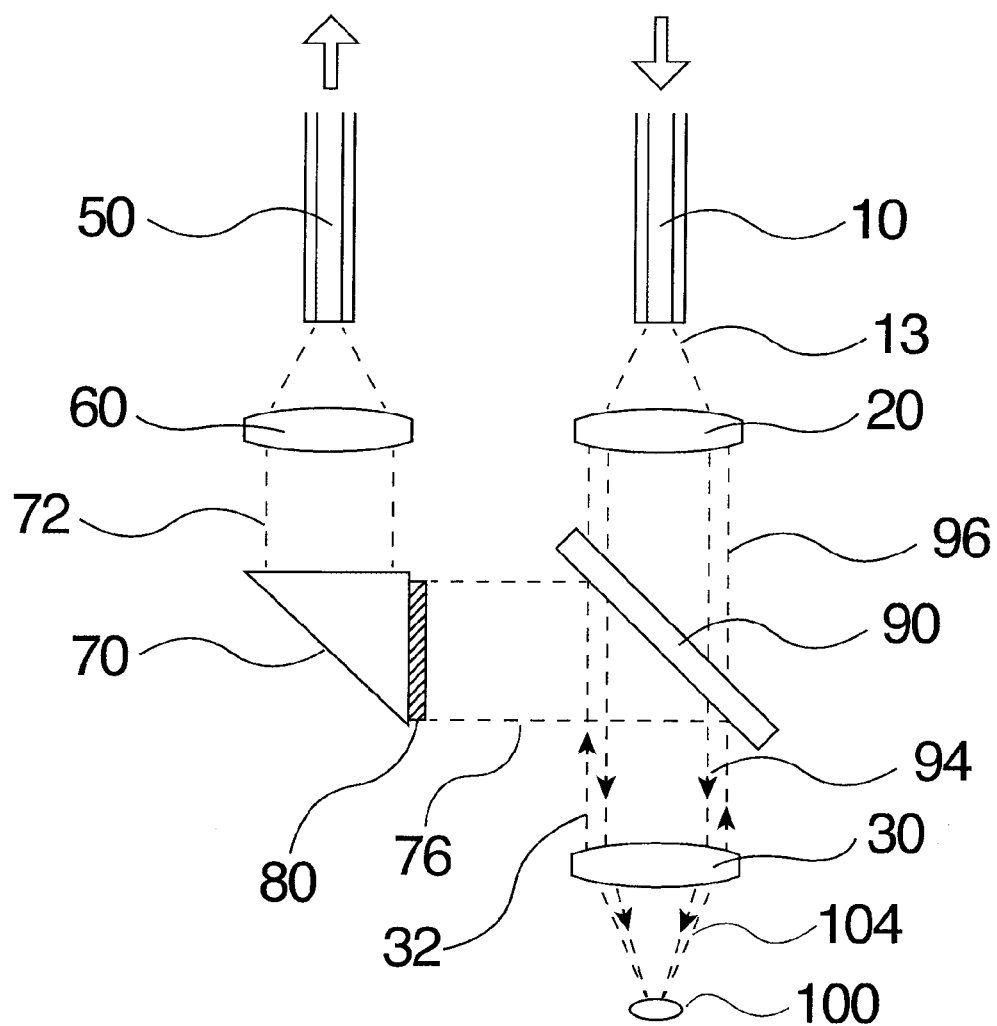
FIG. 1 shows a schematic diagram of prior art fiber optic probe (U.S. Pat. No. 5,112,127; Carraba, et al.).

FIG. 1 illustrates a prior art design of a fiber optic Raman probe disclosed in U.S. Pat. No. 5,112,127 (Carraba et al.). Excitation radiation 13 enters the probe through optical illumination fiber 10, is collimated by lens 20, and impinges on an angled filter 90. The function of this filter is to transmit a narrow band of wavelengths centered around the excitation source wavelength and to reflect all other wavelengths away, thus rejecting any spurious radiation generated inside the fiber by the excitation radiation. Filtered excitation radiation 94 then passes through a first focusing lens 30 and impinges on the sample 100. Back-scattered light 104 from the sample is collected and collimated by the lens 30 to form collimated back-scattered excitation radiation 32 and interacts with the angled filter 90, again. This time, the collimated back-scattered excitation radiation 96 passes straight through the filter, whereas shifted Raman radiation 76 now falls outside the filter's transmission bandpass and is reflected toward a second filter element 80. The second filter element 80 has a function inverse to the first one—it reflects a narrow band of wavelengths centered at the excitation wavelength and transmits radiation outside of that band. Thus, the remaining excitation radiation component of the collected signal, is further attenuated. The collected Raman signal is folded by prism 70 to produce collimated signal radiation beam 72, and coupled into collection fiber 50 by second focusing lens 60.

In this configuration, the illumination 10 and collection 50 fibers are parallel and can be routed together in a single cable. Furthermore, the optical paths are partially overlaid in this design, with the excitation radiation 13 and filtered excitation radiation 94 (collectively the excitation path) being in-line with the sample 100 and the collection path, comprising the shifted 72, and attenuated excitation radiation, folded out. Such arrangement requires very high performance broadband reflector (filter 90) with a narrow transmission band, a difficult component to achieve, to be placed in a tilted position with respect to the beam. which increases stray light within the probe.

Figure 2:
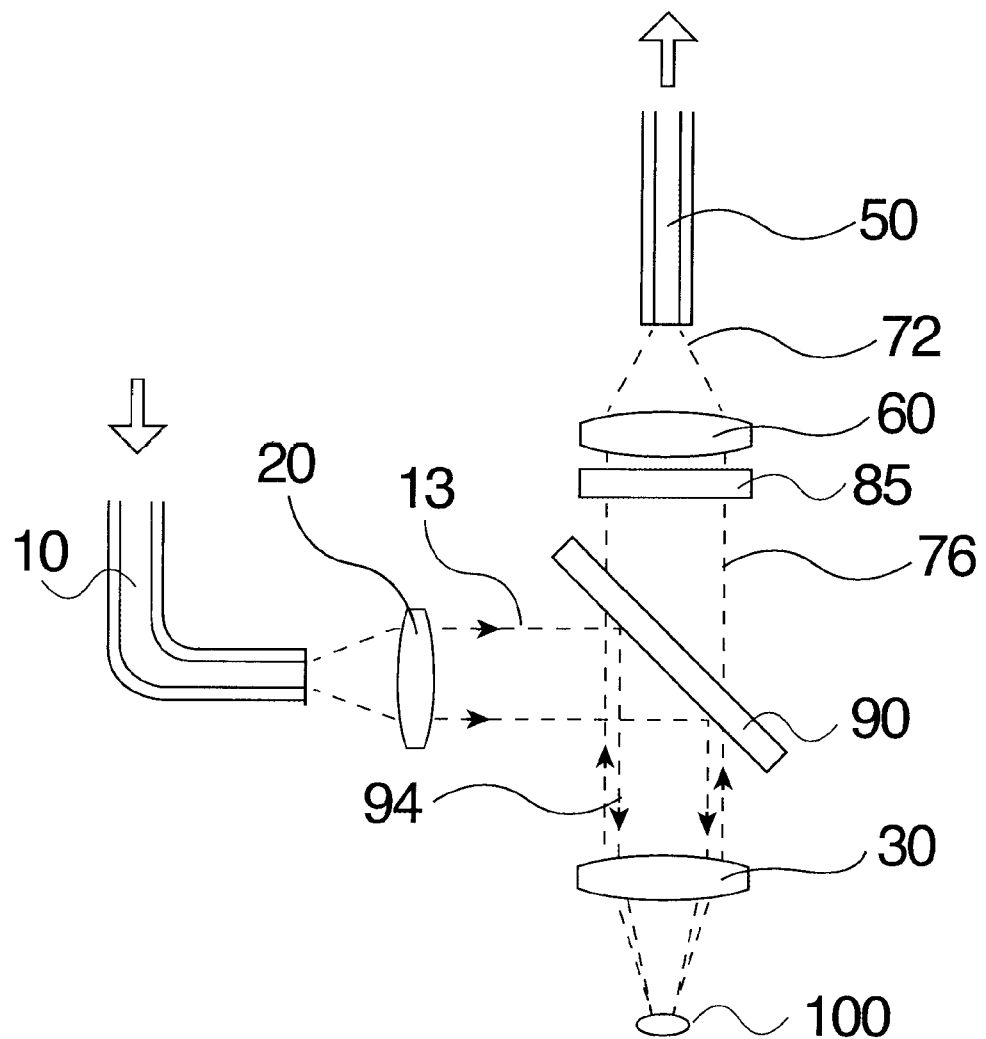
FIG. 2 shows a schematic diagram of prior art probe (U.S. Pat. No. 5,377,004; Owen, et al.).

A prior art device described in U.S. Pat. No. 5,377,004 (Owen et al.) is shown in FIG. 2. In this configuration, the collection path is in-line with the sample, and the excitation path being folded into it. In this case, a narrow band holographic reflector (filter) 90 is employed to fold the excitation beam 13 into the collection path. This component (90) reflects the excitation radiation 13 more efficiently, than the design shown in FIG. 1, resulting in more filtered radiation 94 delivered to the sample. On the return pass, the collected radiation passes through the reflector 90, with only the narrow band around the excitation wavelength 94 being rejected back towards the excitation fiber and the collected shifted Raman signal 76 directed to the collection fiber 50. In such configuration, additional elements could be added to further improve the signal quality, such as a holographic notch filter 85 which further removes any remaining excitation light, leaving substantially only Raman shifted radiation 72.

Figure 3:
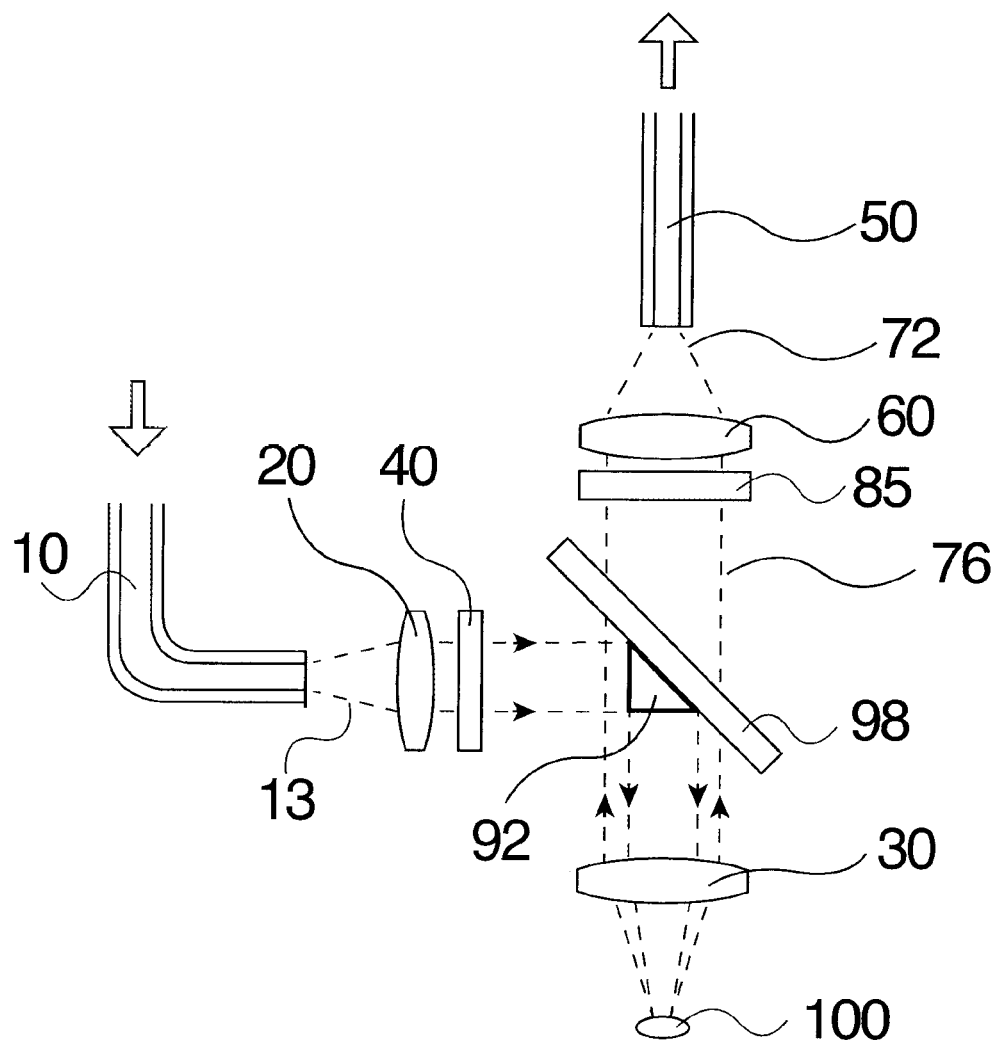
FIG. 3 shows a schematic diagram of prior art probe (U.S. Pat. No. 6,038,363; Slater, et al.).

FIG. 3, show a prior art device described in U.S. Pat. No. 6,038,363 (Slater et al.). In this configuration, the excitation beam 13 is smaller in extent and folded into the collection path using a reflective component 92 such as a mirror or a prism mounted centrally in the collection path on a transparent window 98 so that the two beams share the aperture and not the amplitude as in designs above.

Figure 4:
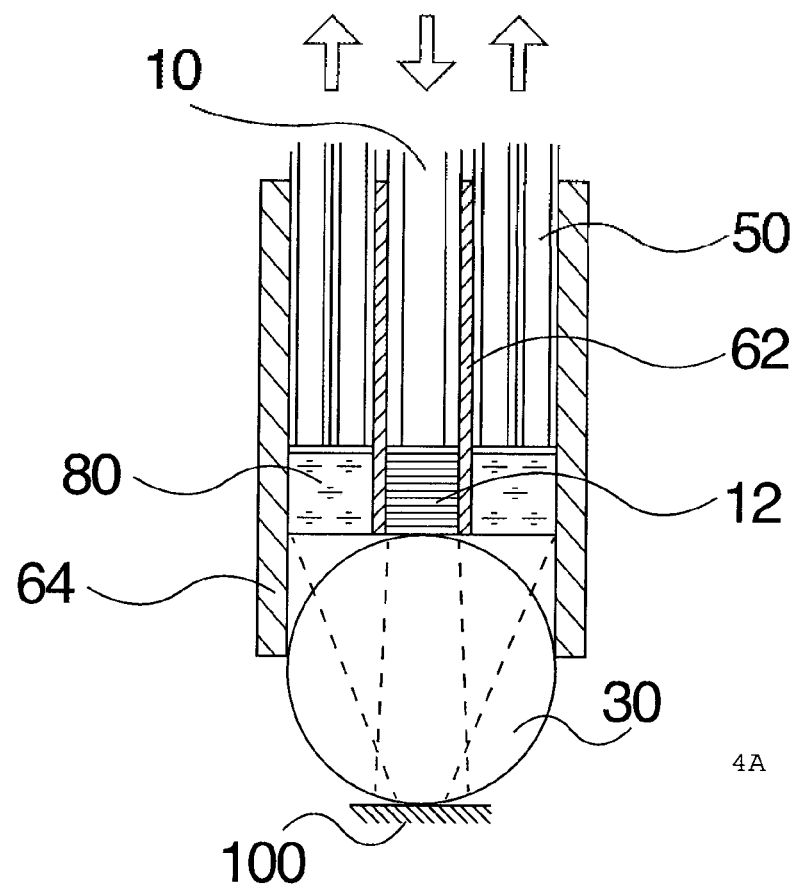
FIGS. 4A and 4B show schematic diagrams of prior art probe (U.S. Pat. No. 7,647,092; Motz, et al.).
Figure 4:
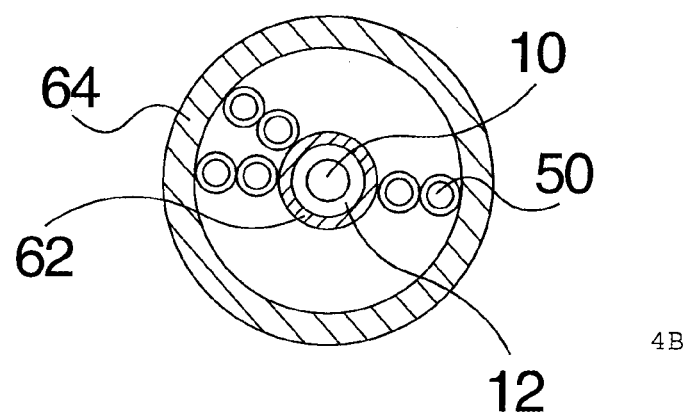

Referring to FIG. 4, a prior art device taught by Motz et al. (U.S. Pat. No. 7,647,092) is shown. In this design, the excitation fiber 10 abuts a small cylindrical narrow band pass filter 12. The excitation channel is optically isolated from the rest of the probe by an optically opaque tube 62. The collection fibers 50 abut an annular narrow band long pass filter 80. The excitation channel is guided through the central hole of the long pass filter. Beam steering and overlap is achieved by using a ball lens 30. The same ball lens is used to transmit excitation energy to a sample, and collect scattered radiation from the sample. The entire probe is packaged within an optically opaque outer tube 64.

Figure 11:
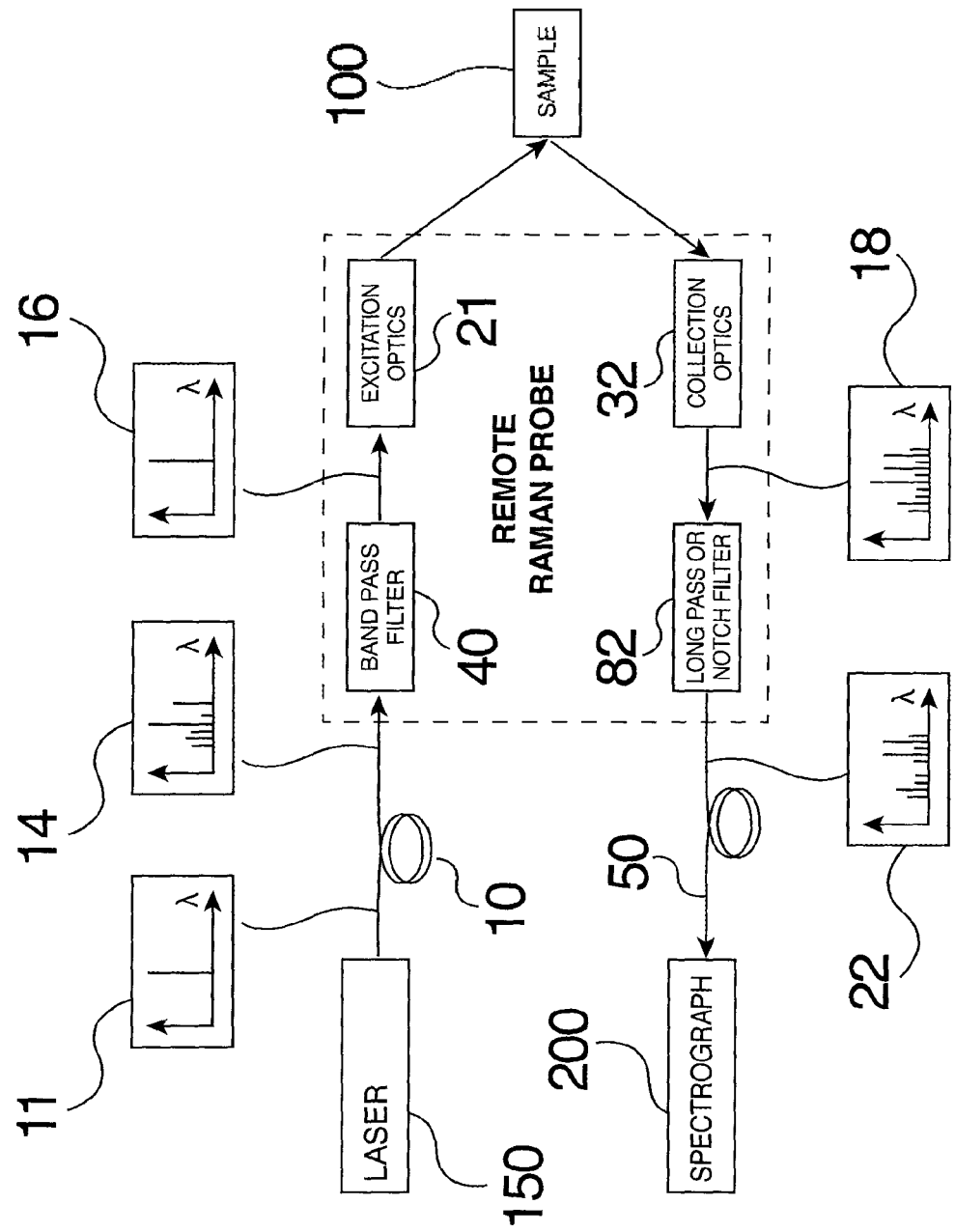
FIG. 11 shows a block diagram of a typical Raman spectroscopy system featuring a generic fiber optic Raman probe.

Referring to FIG. 11 which demonstrates the principal components of a remote Raman spectroscopic system in a block diagram, together with the spectral content at various locations in the system. The excitation radiation is produced by a single frequency laser 150, and coupled into excitation fiber 10. At the input to the fiber, it contains radiation substantially at one wavelength as the spectrum 11 demonstrates. During transit through the fiber 10, laser radiation interacts with the fused silica glass, resulting in silica Raman signal apparent in spectrum 14 as additional peaks around the original excitation wavelength. It then passes through the band pass filter 40 which only transmits a narrow range of wavelengths centered at the laser line, and reflects all other wavelengths, resulting in a spectrum 16 substantially similar to the original laser output. After passing through excitation optics 21 which usually expands and refocuses the beam to desired size and working distance, the beam impinges on the sample 100, where Raman signal of interest is generated. This signal is picked up by collection optics 32 which collimates it. The collected signal consists of original Rayleigh scattered laser radiation as well as the Raman signal as shown in spectrum 18. Generally, the Rayleigh scatter is several orders of magnitude stronger than the Raman signal. If allowed to enter the collection fiber, it would then generate yet more silica Raman which is difficult to filter out without affecting the Raman signal from the sample. Thus, the collected radiation then passes through a laser rejection filter 82, which effectively blocks a narrow band centered around the excitation line, passing only the collected Raman signal shown in spectrum 22. This signal is then coupled into the collection fiber 50 and guided to the spectrograph 200 for analysis.

FIGS. 5A to 5F illustrate the concept of collection and excitation cone overlap for non-imaging fiber probes. FIG. 5A shows a standard optical fiber with core 10 and cladding 15. Light coupled into such fiber (assuming that the entire acceptance cone of the fiber is filled) will exit at the end face (assumed polished flat, at 90 degrees to the axis of the fiber 17) in a symmetric, diverging cone. The angle of divergence 16 is determined by the numerical aperture (NA) of the fiber itself When such a fiber is now polished at an angle, as shown in FIG. 5B, so that its end face is tilted at a certain angle 24 (now less than 90 degrees) from the axis, it behaves like a prism, and the output cone ends up tilted away from the axis toward the sharper tip. The output is no longer symmetrical, but tilted with respect to the axis, away from the angle 19 and diverges slower than in a flat polished fiber. This allows for a certain degree of beam steering.

As the tilt angle 24 decreases (so the tip of the fiber becomes sharper), it reaches the stage where the radiation cannot be confined within the fiber anymore and starts escaping through the sides. In order to confine it, a reflective coating 9 can be applied to the partially polished fiber as shown in FIG. 5C. The radiation reflects off the coating and exits through the flat facet 5 in an even more tilted and flattened cone.

FIGS. 5D to 5F illustrate the concept of overlapping emission and collection volumes and show ways of manipulating the overlap. For example, FIG. 5D shows a standard arrangement of flat fiber bundle of like fibers, with delivery fiber 10 illuminating the horizontally hatched region 23. The collection fibers 50 are typically arranged in a ring around the delivery fiber, but for clarity only the two fibers immediately to the sides of the excitation fiber are shown. The collection fibers each have acceptance cones 34 and 42, indicated with slanted hatching in the figure. As the cones diverge away from their respective fibers, they start to overlap with each other. Several distinct regions can be observed: a region of zero overlap with the excitation cone 23, two regions of partial overlap 54 and 61 where a cone of one of the collection fibers intersects the excitation cone, and finally the dual overlap region 91 where all three cones intersect as indicated by darker hatching. This is the region where the Raman signal generated is captured most efficiently. It is clear that this region begins at a certain distance from the fibers and continues expanding in the direction of propagation of radiation. Unfortunately, the signal of interest is generated most efficiently in the region with highest excitation radiation density, which is in immediate proximity of the excitation fiber end face.

FIG. 5E shows an improvement offered by polishing the collection fibers 50 at an angle as described in discussion of FIG. 5B, above, and arranging them in a ring around the flat polished excitation fiber 10 so that all sharp points are in closest position to the central fiber. The collection cones 34 and 42 (indicated again with slanted hatching) are now tilted toward the axis of the excitation fiber, resulting in a reduced zero overlap zone. The other single overlap zones 54, 53, 61, 63 are smaller and located closer to the excitation fiber 10. In this example, the dual overlap zone 91 is of a finite volume. In this configuration, significantly more signal will be collected from the sample, with better depth discrimination than previously.

FIG. 5F illustrates additional improvement offered by partially polishing the collection fibers 50 at an angle and coating the beveled face with a reflective surface 9 as discussed above for FIG. 5C. In this example, the dual overlap zone is smaller than that as shown in FIG. 5E, and positioned closer to the end face of the excitation fiber 10, thus increasing the quantity of signal generated. The collection cones 34 and 42 are tilted at such angles that they intersect with the excitation cone 23 over a limited distance only, resulting in clearly limited depth response of the probe. All the overlap regions 54, 53, 61, 63 and 91 are smaller than in the previous cases shown in FIGS. 5D to 5E.

Figure 6:
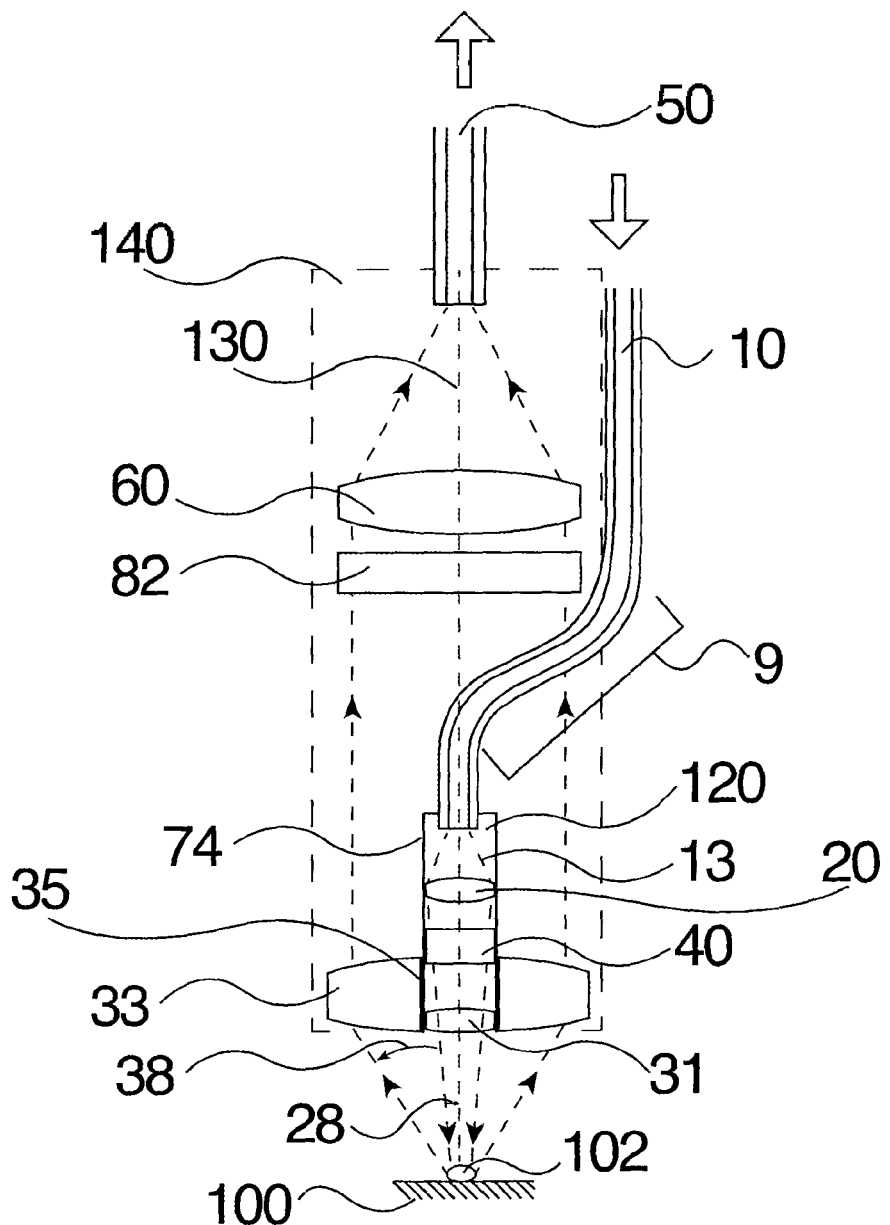
FIG. 6 shows a schematic diagram of a non-limiting example of a fiber optic probe of the present disclosure.

FIG. 6 shows a schematic view of the optical layout of an example of the present disclosure. This embodiment is particularly configured for Raman spectroscopy measurements, the design principles underlying this configuration are applicable to other measurement modalities as well. Some of those modalities may require no filters at all, or different types of filters, for example. It will be clear to those skilled in the relevant arts that the choice of particular filters or other optical elements does not affect the scope of the disclosure.

The excitation radiation 13 is delivered to the probe by means of delivery light guide (excitation fiber) 10. This light guide may be comprise of one or more optical fibers of any suitable type, preferably it is a fused silica, multimode step index fiber. Its core diameter should be appropriate for transmitting radiation generated by the source employed for excitation, and generally between 10 and 1500 µm or any amount therebetween, for example 10, 20, 25, 30, 40, 50, 75, 100, 150, 200, 250, 300, 350, 400, 450, 500, 550, 600, 650, 700, 750, 800, 850, 90, 1000, 1100, 1200, 1300, 1400, 1500 µm or any amount therebetween, with numerical aperture of between 0.06 and 0.53, or any value therebetween, for example 0.06, 0.11, 0.16, 0.22, 0.26, 0.28, 0.34, 0.37, 0.39, 0.48 or any value therebetween, in such combination that a required spot size can be generated at the sample. Other types of light guides, for example, but not limited to single mode fiber, photonic crystal fiber, fibers made of different materials than fused silica, and also bundles of such fibers, and the like, may also be used as dictated by the desired excitation spectral content and the source used; these alternatives are included within the scope of the present disclosure.

The delivery light guide 10 is routed along the outside of the collection optical system (outlined by dashed line 140) and suitably formed (e.g. 9) to bring the light guide into the middle of the probe so it is substantially centered and substantially coaxial with the optical axis 130 of the collection system. In an embodiment, the method of forming the excitation multimode fiber is to encase it in a small diameter tube and to bend it into appropriate sigmoid shape. However, other approaches will be readily apparent to those skilled in the art, such as using one or more folding elements, one or more reflective elements, or one or more waveguides, instead of the bent fiber.

At this point the light guide 10 is coupled to the excitation optical system sheathed in optically isolating tubular housing (outlined by dashed line 120). The excitation beam 13 delivered by the light guide 10 diverges and impinges on the collimating element 20. Now collimated, it traverses the band pass filter 40 which eliminates the spurious silica Raman signal generated within the delivery light guide 10. Filter 40 is recommended when using a probe configured for Raman measurements, but this element may be optional when using other modalities for example, but not limited to, light scattered spectroscopy, fluorescent spectroscopy, reflectance spectroscopy, time-based measurements (monitoring signal change over time) and the like. The excitation beam then passes through a focusing element 31 and is focused into beam filling a solid angle 28 and illuminating a spot 102 on the sample 100. In the example shown, the entire excitation optical system 120 contained in its optically opaque tubular housing 74 is positioned in a circular aperture 35 of appropriate size realized in the front optical element 33 of the collection optical system 140. In this manner, the two systems are optically isolated. Thus, the optical path of the excitation beam passes through part of the collection optical path without interacting with it.

As would be recognized by those skilled in the art, the circular aperture in the first collection element 33 can be achieved by many processing methods for example, but not limited to, laser machining, ultrasonic milling, diamond drilling, chemical etching, and others. An equivalent element can also be built from two or more segment parts that when assembled together form an annular component with a circular aperture.

While in the embodiment shown, the delivery channel is positioned substantially coaxially within the collection channel, this is not a requirement. Some measurement modalities may require off-axis illumination. In such a case, the aperture hole 35 can be located anywhere within the physical extent of the first collection element (front optical element 33) of the collection optical system, and its mechanical axis does not need to be parallel to the optical axis of the collection optical system.

In the example shown, the circular aperture 35 in the first collection element 33 forms a central obscuration area in the collection system. In other embodiments of the disclosure, where the physical dimensions of the fiber optic probe are not critical, it may not be necessary to minimize the relative size of the obscuration area with respect to the overall area of the collection elements. For example, a hole 1 mm in diameter in a 10 mm diameter element occupies just 1 percent of the whole area, with negligible effect on the overall throughput. However, for applications where miniaturized embodiments may be required, such as in-vivo endoscopy, there may be practical limitations to the dimension of the aperture. The size of the hole is driven by the diameter of the excitation channel components, and of the band pass filter in particular.

For endoscopic applications, it may be desirable to have a probe which can be inserted into a standard endoscope instrumentation channel, which is typically on the order of 2 mm in diameter. The actual probe should be a little smaller, 1.8 mm for example or 1.0 mm or 0.5 mm. Taking the isolation between the two channels into account, the hole into which a 500 μm diameter excitation channel would fit would be about 700 μm, resulting in an obscuration factor of 15% of the total collection area.

It is possible that other techniques allow for successful manufacturing of even smaller filters with adequate performance. Ultrafast laser micro-machining holds a lot of potential in this field, among others. The disclosure herein is not connected to any particular size or measurement.

Now, continuing with FIG. 6, an embodiment is shown wherein the excitation radiation interacts with the sample 100, resulting in scattered photons being emitted in all directions. The annular element 33 collects the scattered signal together with back-scattered excitation radiation from the solid angle 38 and collimates it. The signal passes through an excitation rejection filter 82 and is focused into the collection light guide 50. The collection light guide may be comprised of one or more optical fibers of similar type to those employed in the delivery light guide 10, but may contain more fibers. These fibers may also have a different core diameter and numerical aperture, as needed.

In the embodiment shown, all collimating and focusing elements 20, 31, 33 and 60 are achromatic doublet lenses. However, it will be obvious to those skilled in the art that comparable performance can be obtained from many alternative optical components for example, but not limited to, aspheric lenses, ball lenses, GRIN lenses, diffractive optics, holographic optical elements, curved mirrors, and the like, without changing the scope of the present disclosure. For improved performance, some of the doublet lenses could also be replaced with more complex compound lenses such as triplets or microscope objectives. Again, such modifications are within the scope of the present disclosure.

In the embodiment shown in FIG. 6, since the two optical beam paths are isolated, they can be configured independently to optimize their throughput. The two beams are focused to a spot 102 of the same size at the sample. However, the angular extent of the two beams can be different. In the delivery channel (illuminating fibre 10), the construction parameters of the delivery optical system 120 can be selected so the image of the illuminated spot 102 on the sample matches the delivery light guide area and divergence angle.

On the collection side, the parameters of the collection optical system 140 can be selected so the image of the illuminated spot 102 on the sample matches the collection bundle area and collection angle.

Also, it can be seen that the collection optics do not pick up the central section of the possible collection cone as it is blocked (centrally obscured) by the delivery channel. While this lowers the amount of collected signal, as discussed above, it also blocks the Rayleigh back-scattered excitation radiation from entering the collection optics and confines the overlap zone of the two beams to a small volume near the common focal spot.

An additional advantage is present for reflective samples, which for normal illumination redirect a significant part of the excitation radiation back toward the source. In the present embodiment, this back reflected portion of radiation impinges onto the delivery channel, and not onto the collection channel, further reducing the probe background signal.

Another property of the centrally obscured system design as described herein is the requirement for "stand-off". The probe as described herein requires a certain minimal distance between the delivery and collection systems and the sample, as no signal can be collected from the dead zone created by the obscuration. This enables measurements through containers or vials where signal is collected only from the sample at a certain distance, while the packaging or container remain essentially invisible to the probe.

It should also be noted that because the central obscuration and the bent fiber tube are placed in the pupil space of the collection optics they do not form sharp images at the collection light guide input face, but rather reduce the overall flux reaching the bundle. This results in even illumination across the collection light guide which can then illuminate the entrance slit of the spectrograph uniformly.

The optically opaque tubular sleeve may be disposed in a longitudinal hole through the front component of the second (collection) optical system, the central axis of the hole being substantially collinear with the central axis of the second optical system and the distal end of the optically opaque tubular sleeve substantially coincident with the front surface of the front component so that the optically opaque tubular sleeve partially obscures the back component of the second optical system so that the portion of the illumination beam reflected specularly by the sample travels back into the first (delivery) optical system and is not collected by the second optical system, thus further reducing the background signature of the probe.

The probe may further comprise an optically transparent window element having a central axis and a thickness, disposed between the front optical element of the collection, delivery, or both the collection and delivery optical system and the sample, for isolating the probe body from the sample.

As would be evident to one of skill in the art, the optical probe design described above may be used for particular purposes and applications to determine spectral information from a sample. For example, the probe can be adapted for use in industrial applications such as in-line process control. It could also be adapted to applications in hostile or hazardous environments containing inhospitable conditions, radiation, toxic chemicals, and infectious agents. It could also be adapted for use in confined spaces such as in-vivo endoscopy, or catheter use for medical diagnostic applications.

The optical probe design described in the present disclosure may also be adapted for applications involving other types of light measurements involving scattered light, such as fluorescence or reflectance measurements. Skilled practitioners in the relevant arts could simply change the excitation light source and the optical filters of the current embodiment to achieve those other modalities.

Figure 7:
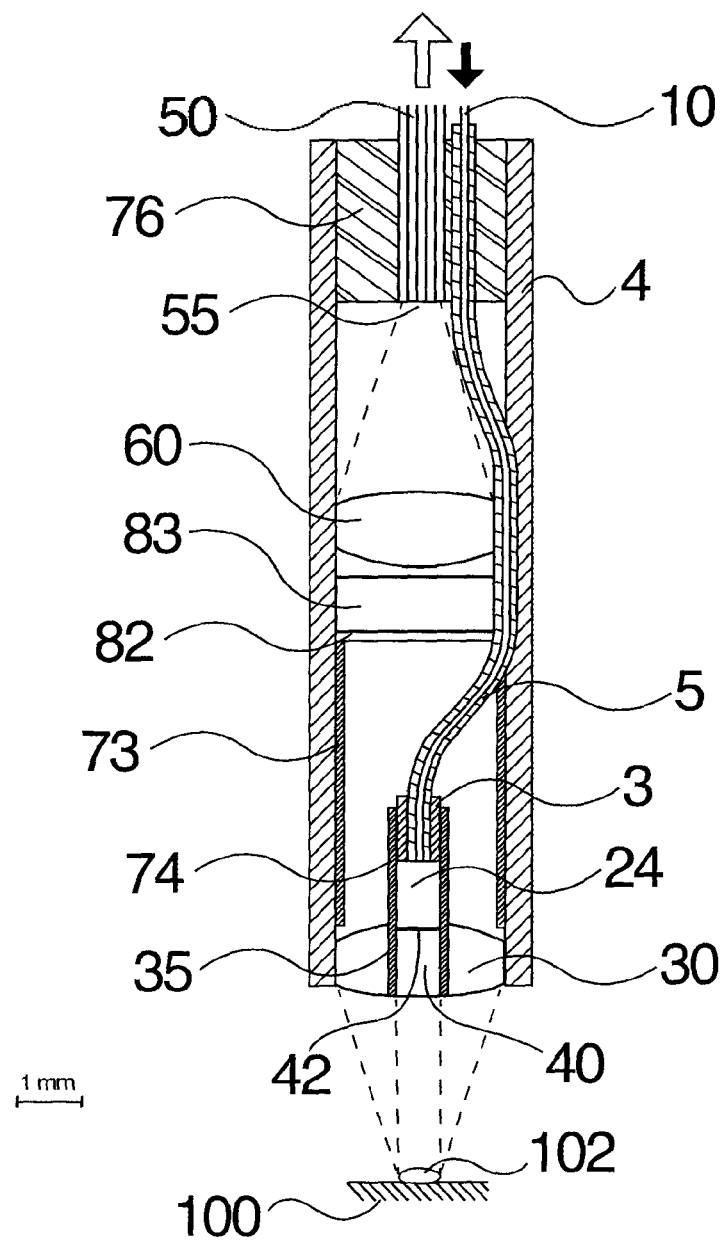
FIG. 7 shows a cross-sectional view of a non-limiting example of a fiber optic probe of the present disclosure, shown approximately to scale, in which the excitation beam is substantially collimated.

In the example shown in FIG. 7, a delivery optical system comprises an excitation fiber 10, for example, a 100 μm core, 120 μm cladding ultra low $OH^-$ step index fiber, designed for transmission in the visible and near-infrared spectral region. In order to shield the rest of the probe from the excitation radiation propagating inside it, the fiber is jacketed in black polymer throughout the probe, and sheathed in a small diameter stainless steel tube 5 of approximately 300 μm diameter over the last 10-15 mm inside the probe body 4. The tube 5 containing the excitation fiber 10 is bent into a sigmoid shape with shallow bends respecting the bending radius of the fiber inside. The thicker cladding of the fiber (120 μm) reduces the bending losses of the excitation fiber. With this configuration transmission of over 85% of the incident excitation radiation can be achieved. The tube 5 is terminated with a small ferrule 3 which centers the fiber 10 on the optical axis of the delivery optical system.

The delivery optical system as shown in the example of FIG. 7, comprises a gradient index (GRIN) lens 24 which is selected to expand and substantially collimate the excitation radiation, producing a beam approximately 600 μm in diameter, combined with a dielectric stack laser line bandpass filter 40. The filter component may be selected to effectively clean up 785 nm excitation wavelength and machined to a diameter of approximately 1 mm. It is mounted with the filter surface facing the GRIN lens, with a small air gap separating the two. The two components are packaged together in a steel tube 74 approximately 1.27 mm in diameter and 6 mm long which serves simultaneously as a structural support for the excitation optical system and as an optical isolator between the collection and excitation channels. The excitation fiber 40, tube 5 and ferrule 3 assembly is inserted into the tube 74 and bonded to the back face of the GRIN lens 24.

The complete excitation channel assembly is placed and fixed in the aperture 35 of the front collection lens 30 so that their front surfaces coincide. The annular collection lens 30 is for example, 3 mm in diameter with a 1.27 mm diameter hole through it. Thus, the excitation channel obscures almost 18 percent of its surface. Arranged this way, the two beams overlap at approximately 4.3 mm from the probe face, and form a spot 102 with diameter of approximately 600 μm.

The space required for the bent excitation fiber to exit the collection channel is created by a spacer 73 inserted between the collection lens 30 and the Rayleigh rejection filter (excitation rejection filter) 82 deposited on substrate 83. This spacer 76 is slit lengthwise, with the excitation fiber tube 5 placed lengthwise through it. In this way the tube does not add to the overall diameter of the probe. The now filtered signal containing only useful Raman signature is focused onto the distal end face 55 of the collection light guide (collection fiber) 50 by a focusing lens 60.

In this embodiment, the two lenses in the collection path (30 and 60) are substantially identical, except for the circular hole realized in the center of one of them (30). Thus the collection system performs 1 to 1 imaging of the spot on the sample onto the distal end face 55 of the collection bundle. The collection bundle is comprised of 19, 100 μm core, 110 μm fibers tightly packed into a circular aperture with diameter of approximately 600 μm, matching the spot size on the sample.

The most frequently used optical fibers are of cylindrical shape with round cross-sections, and the most advantageous fashion to arrange a plurality of such fibers is in a bundle disposed of hexagonally packed fibres, which minimizes the losses in dead spaces between the individual fibers. In recent years, optical fibers with non-circular cross-sections have been produced. Additional gains in efficiency may be realized by replacing circular fibers of the collection bundle with square, hexagonal or octagonal fibers.

The collection light guide is held in a steel ferrule 76 which is fixed into the main housing 4. In this example, the probe tip is approximately 4 mm in diameter and about 35 mm long.

At the distal end of the probe, at the entrance to the spectrograph, the 19 collection fibers may be rearranged into a linear array approximately 2.3 mm in height and 100 μm wide.

The components for both optical systems are selected in such a way that standard optical techniques of lens barrel assembly can be used, in which the lenses, filters and spacers are simply dropped into the sleeves in appropriate order and held in place by adhesive. Optically opaque adhesives are employed where required throughout the assembly.

Figure 8A:
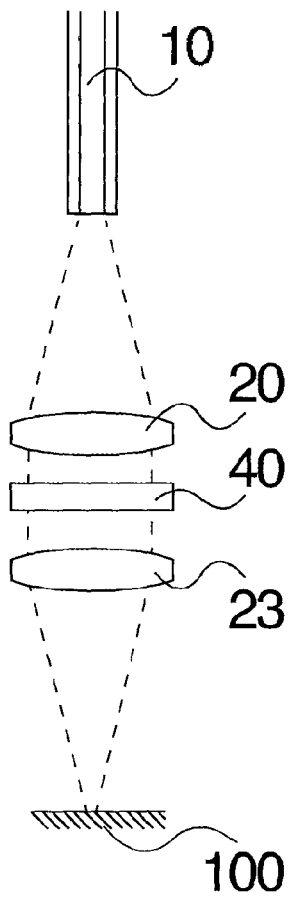
FIGS. 8A to 8C show schematic diagrams of alternative embodiments of the excitation optical sub-system of the present disclosure, and show various ways of expanding and focusing the excitation beam.
Figure 8B:
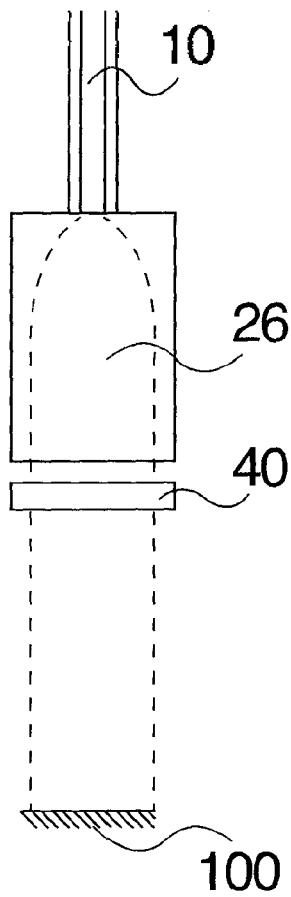
Figure 8C:
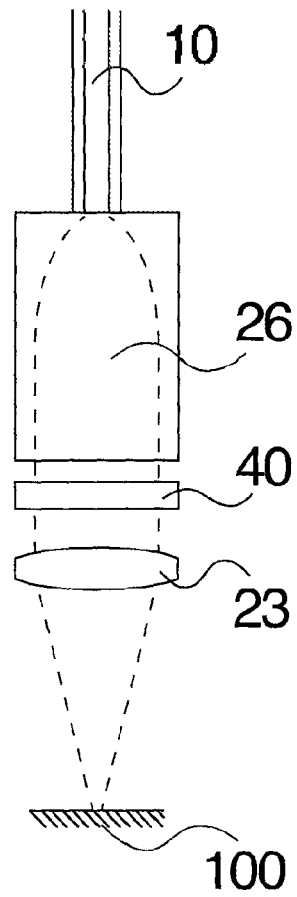

FIGS. 8A to 8C show several alternative embodiments of the excitation optical system. For clarity, the bent section of the delivery fiber is not indicated. FIG. 8A illustrates an example in which the excitation radiation is delivered by fiber 10. Upon exiting the fiber it diverges and impinges on lens 20 which substantially collimates the beam. It then passes through the band pass filter 40 and is focused onto the sample by lens 23. By varying the parameters of the two lenses 20 and 23, various magnification ratios and spot sizes can be achieved as required.

FIG. 8B illustrates an alternative embodiment as used in the embodiment described in FIG. 6. In this case the collimating lens 20 (of FIG. 6) is replaced by a suitably selected quarter period GRIN lens 26. This type of component is particularly suitable for miniaturized probes as its cylindrical shape simplifies assembly and alignment. The GRIN lens 26 produces substantially collimated beam which then passes through the band pass filter 40 and continues onto the sample 100, resulting in a spot size of approximately 500 μm.

FIG. 8C illustrates a focused version of the assembly of components used in FIG. 8B, where the collimated beam produced by the GRIN lens 26 is refocused onto the sample by focusing lens 23. It will be clear to those skilled in the relevant arts that other combinations of refractive lenses, GRIN lenses, or other suitable optical components can be employed to achieve the same function within the excitation channel.

Figure 9A:
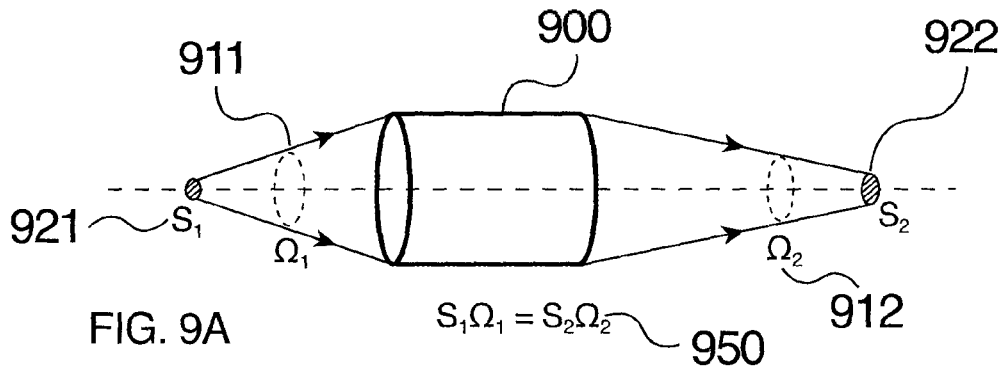
FIGS. 9A to 9C show a schematic diagram to demonstrate the principle of étendue and the effect of shortening the collection lens focal length on the collection angle and spot size.
Figure 9B:
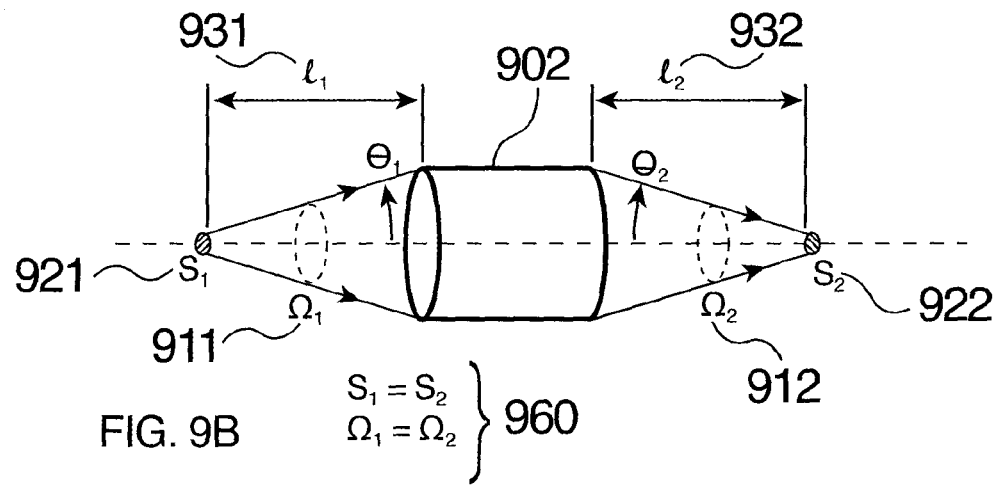
Figure 9C:
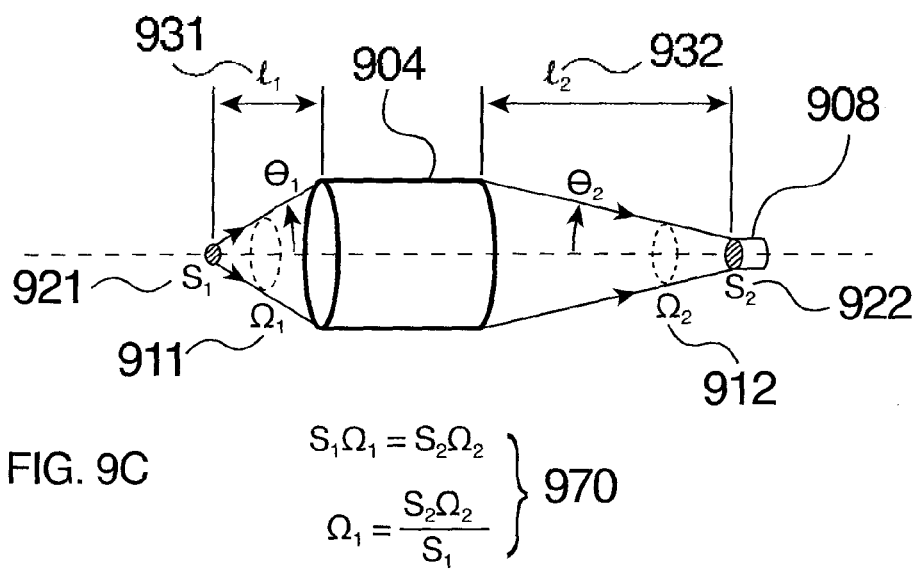

FIGS. 9A to 9C demonstrate the principle of &endue as it applies to the current disclosure, illustrating how parameters of the excitation and collection optical systems can be selected independently to optimize the overall system throughput.

FIG. 9A shows a schematic representation of an arbitrary optical system 900 which images an object 921 with area $S_1$ into an image 922 with area $S_2$. As seen by the optical system, the object subtends a solid angle 911, indicated by $\Omega_1$, and the image subtends a solid angle 912, indicated by $\Omega_2$. Étendue, which represents the light gathering capability of this optical system, is the product of the object area by the solid angle. In a perfect optical system, étendue of the image should be identical to the étendue of the source, as indicated by equation 950. In practice, the étendue of a complex optical system consisting of multiple components is limited to the component with the lowest étendue.

FIG. 9B shows a schematic representation of a specific optical system 902 characterized by in that it images an object 921 into image 922 with unit magnification. In this example, the solid angles $\Omega_1$ and $\Omega_2$ as well as areas $S_1$ and $S_2$ are equal, as shown by equations 960. In this particular system, working distance 931 $l_1$ and image distance 932 $l_2$ are also equal.

FIG. 9C shows how optical system parameters (focal length, object size, magnification, working distance) can be selected to match a particular application. An object 921 has a particular area $S_1$, and a receiver 908 has a particular area 922 $S_2$ and acceptance angle $\Theta_2$ corresponding to a solid collection angle 912 $\Omega_2$. In order to preserve étendue, the optimal optical system 904 can then be designed with solid collection angle 911 $\Omega_1$ defined by equations 970. Satisfying these equations defines the other system parameters, such as magnification and focal length.

As an example, the optical system can be configured in such a way that the image generated at the receiver 908 has surface area $S_2$ exactly four times that of the object area $S_1$. This means that the image solid collection angle $\Omega_2$, will be ¼ of the object solid angle $\Omega_1$. One of the ways of achieving this is to shorten the distance $l_1$ between the object and the optical system as shown in FIG. 9C. In this particular case the distance $l_1$ would be half of the distance $l_2$ between the optical system and the receiver.

An advantage of the present invention is that both the excitation and collection channels feature independent and separate optical systems, each of which can be independently configured to work optimally for a given application.

Figure 10A:
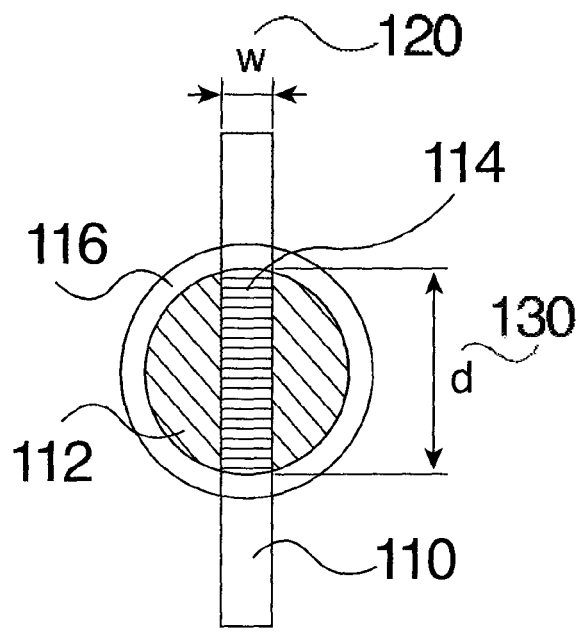
FIGS. 10A to 10C show schematic diagrams that illustrate an advantage of forming the spectrometer-end of the collection fiber bundle in a linear slit format approximating the size of the spectrometer input slit.
Figure 10B:
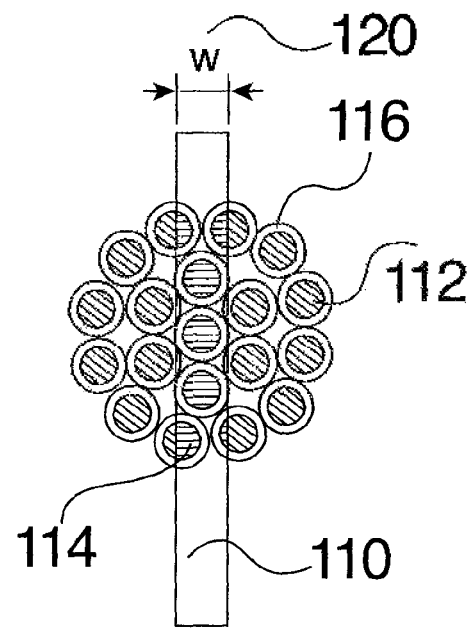
Figure 10C:
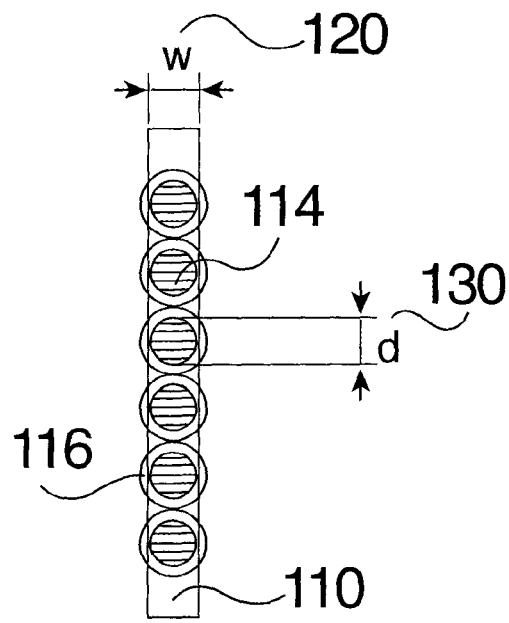

FIGS. 10A to 10C show several possible realizations of coupling the collection light guide into the input slit of a light measuring device, typically a dispersive spectrograph. A narrow input slit realized in an optically opaque substrate is typically disposed in the direction orthogonal to the dispersion axis of the spectrograph. The spectrograph forms an image of the input slit for each wavelength present. A superposition of all these images results in a spectrum in the image plane of the spectrograph, where it can be registered by a suitable detector. The width of the slit is affects the spectral resolution of the spectrograph—the narrower the slit, the higher the resolution. However, narrowing the slit reduces the amount of light reaching the image plane.

FIG. 10A shows an example where the collection light guide consists of a single large core optical fiber 116 with a core 112 of diameter d 130 which is disposed in contact with a rectangular slit 110 of width w 120. The diameter of the fiber is larger than the width of the slit, which results in regions of the fiber core hatched diagonally being blocked by the slit. Only radiation from the horizontally hatched region 114 can actually enter the spectrograph, resulting in inefficient coupling of collected light into the spectrograph.

Replacing the single large core fiber with multiple smaller core fibers is shown in FIG. 10B. In this case, the coupling efficiency is comparable to the situation described in FIG. 10A. Only some of the cores, indicated by horizontal hatching within the region 114 overlap the slit 110 and are coupled into the spectrograph.

FIG. 10C shows an alternate way of coupling radiation from a collection light guide disposed of plurality of optical fibers 50 with core diameter d 130. The fiber diameter d is selected to closely match the width w 120 of the slit 110. The fibers of the collection bundle are disposed in a closely packed linear arrangement, its longer direction aligned with the length of the slit. In this arrangement, radiation from all cores can pass through the slit and is coupled into the spectrograph efficiently, provided that the numerical aperture of the optical fibers matches the input numerical aperture of the spectrograph.

Figure 12A:
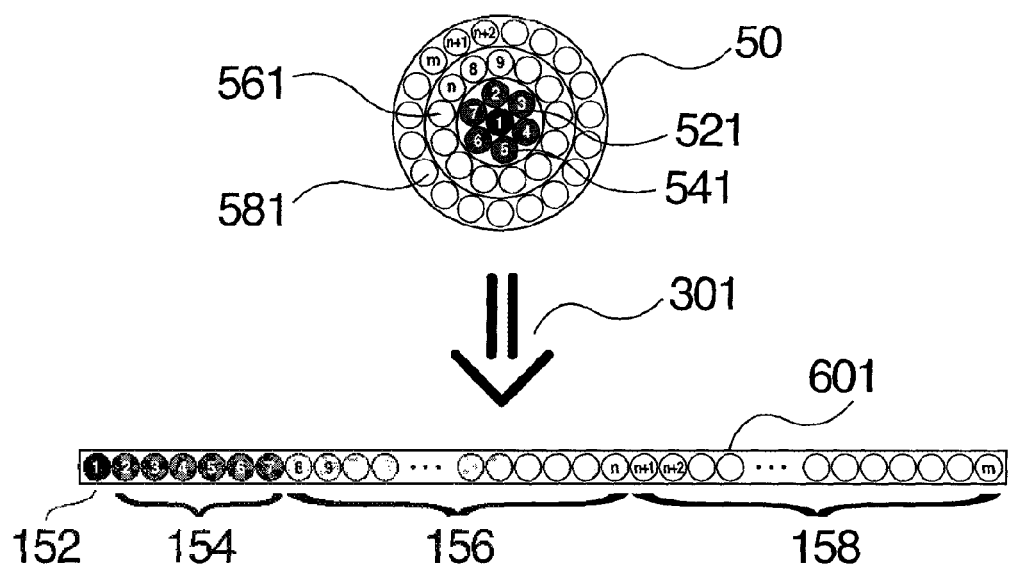
FIGS. 12A and 12B show schematic diagrams of two methods of performing imaging spectroscopy by mapping the successive fibers from the collection bundle to sequential locations within the linear output slit.

Turning now to FIG. 12A, which shows a non-limiting example of efficient coupling of radiation collected by the collection light guide into a spectrograph, wherein the collection light guide 50 is comprised of a plurality of like individual fibers arranged in a tightly packed hexagonal bundle. In such a bundle, concentric rings of fibers can be identified, with the central fiber 521 identified by numeral 1 surrounded by 6 fibers in the second ring 541 identified by numerals 2 to 7, 12 fibers in the third ring 561 identified by numerals 8 to n and so on. The number m of fibers present in the collection light guide is typically a compromise between the transverse size of the image generated by the collection optical system of the probe and by the height of the input slit of the spectrograph, which in turn is related to the detector used.

At the proximal end of the collection light guide, the bundle of fibers 50 is rearranged into a closely packed linear array 601. Additionally, the individual fibers are mapped from the round bundle to the linear array by a mapping process 301 so that fibers from the successive rings in at the distal end are placed next to each other in an ordered sequence. Thus, the central fiber 521 is placed at one end of the array at 152, followed by fibers 2, 3, . . . , 7 of the first ring 541, indicated as the region 154, followed by fibers 8 to n (of the second ring 561) indicated as the region 156 and so on up to fiber m on the right side of the array.

An advantage of such an arrangement is that the fibers which are placed close to each other at the distal end of the lightguide are also close at the proximal end. Thus, the cross-talk between fibers collecting radiation from different regions of the image formed by the collection optical system is minimized.

Another advantage of such an arrangement is that knowledge of the mapping order 301 allows for an approximate reconstruction of the spot on the sample viewed by the probe, thus providing some imaging capabilities to the probe, limited only by the number of individual fibers employed.

Figure 12B:
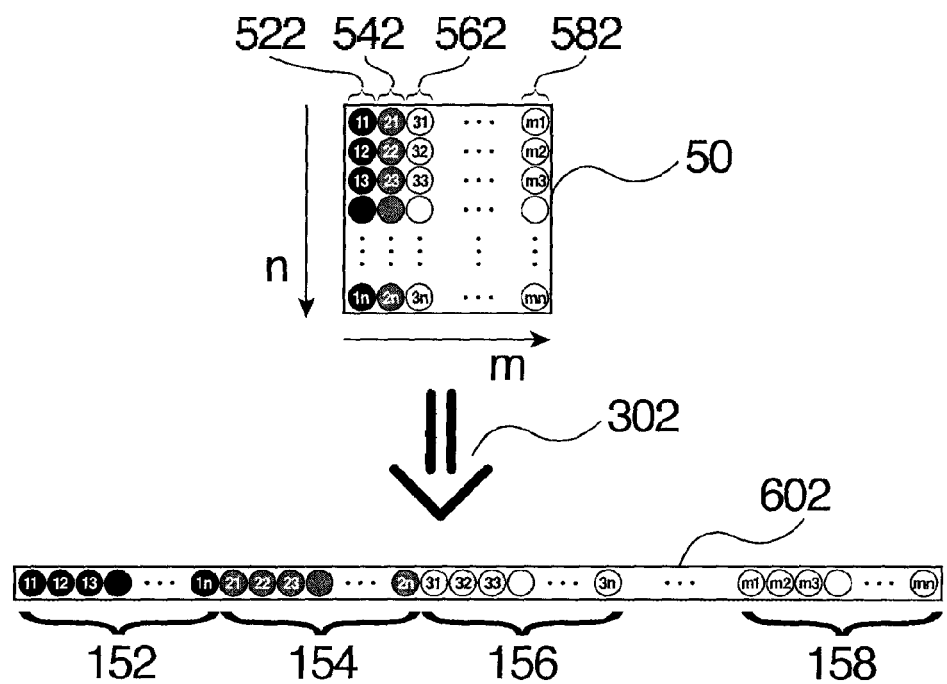

FIG. 12B shows an alternative arrangement in which the individual fibers at the distal end of the collection bundle 50 are arranged in a closely packed rectangular array of m×n fibers. The first n fibers indicated by numerals 1 to n are disposed in the leftmost column 522 of the array, with the second n fibers, indicated by numerals 21 to 2n in a column 542 immediately to the right, and so on until the rightmost, mth column 582 containing fibers m1 to mn. The fibers are again rearranged at the proximal face of the bundle by a mapping process 302, so that the fibers from each column are disposed sequentially in the linear array 602, with the first n fibers from the column 522 now in the leftmost segment 152 of the array, the second n fibers from the column 542 in the neighboring segment 154 and so on until the last n fibers from column 582 are arranged in the mth segment 158 on the right.

Such an arrangement is particularly advantageous for fibers with square or rectangular geometry, where more efficient packing with almost no voids between fibers can be achieved. However, even for bundles comprised of a plurality of circular fibers there is an advantage, as the measured patch on the sample is now rectangular, making the image reconstruction more straightforward.

Turning now to FIGS. 13A to 13D which demonstrate several alternative embodiments of the current disclosure that may be adapted to different applications. For simplicity, all of the figures show schematic views of the various embodiments with like elements identified in like manner. The collection optical system 140a and delivery optical system 120a are represented in a simplified way as distinct volumes, the excitation system fully contained but separate from the collection system. Radiation gathered by the collection system is formed into a focused beam (collection beam) 56 which impinges on the collection light guide 50.

Figure 13A:
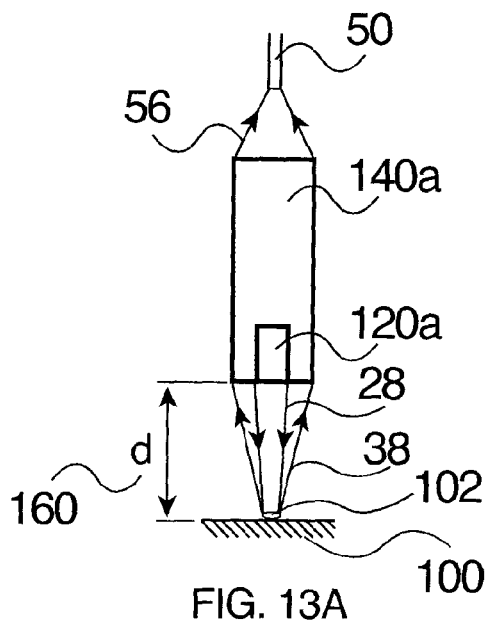
FIGS. 13A to 13D show schematic diagrams of several alternative examples of the fiber optic probe of present disclosure configured for various measurement requirements.

FIG. 13A shows a schematic view of the preferred embodiment described in FIGS. 6 and 7 above. The excitation beam 28 exits the delivery optical system 120a and is focused into a spot 102 on the sample 100. This spot matches the object size of the collection optical system 140a at a standoff distance 160 d. The back-scattered radiation from the sample forms a beam 38 matching the collection system collection solid angle. This radiation is formatted into a collection beam 56 and focused on the collection light guide 50. This configuration is well adapted to measurements of highly scattering, light absorbing samples such as small particles of solids, pills, drops of opaque liquids and many others.

Figure 13B:
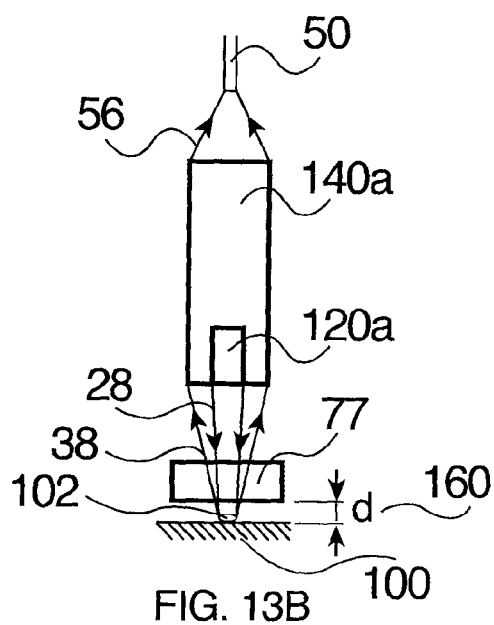

FIG. 13B shows a schematic view of another embodiment which is advantageous for measuring samples which require close contact to the probe. The standoff distance d 160 is reduced in this embodiment by adding an optically transparent window 77 in the front of the probe. The excitation beam 28 is then focused into a spot 102 just beyond the outer surface of the window. The window does not contribute to the background signal of the probe because it is placed in the shadow of the delivery optical system, and any surface reflections from the window return back into the delivery channel itself. This embodiment works well with powdered solid samples and biological tissues such as skin, bone and others.

Figure 13C:
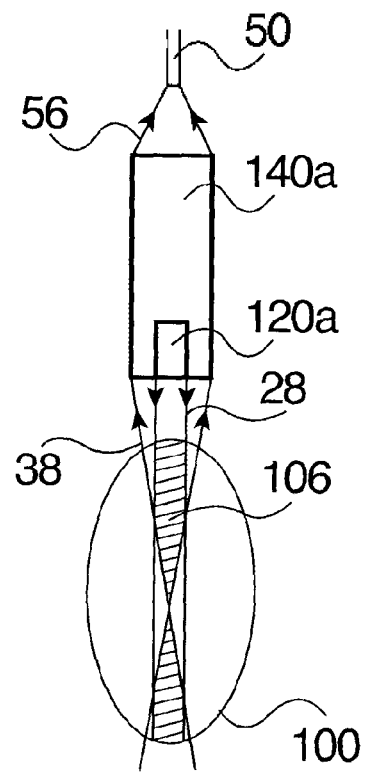

FIG. 13C shows a schematic view of another example which is advantageous for measuring weakly scattering samples such as optically clear liquids and gases. The delivery optical system 120a is constructed to produce a substantially collimated excitation beam 28. The collection optical system 140a is configured to have a long working distance so that the excitation and collection volumes overlap over a significant path length through a low scattering sample 100. This overlap volume is illustrated by diagonally hatched region 106. Back scattered radiation generated throughout the region 106 is gathered by the collection optical system 140a.

Figure 13D:
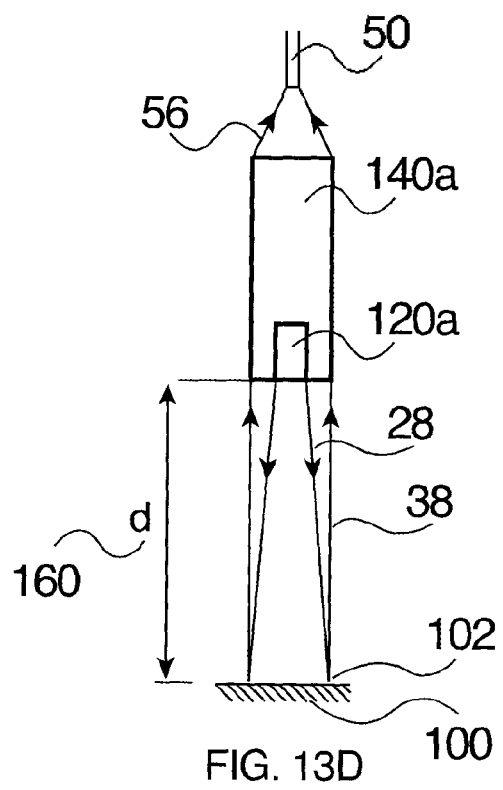

FIG. 13D shows a schematic view of yet another embodiment in which the delivery optical system 120a is constructed to produce a slowly diverging excitation beam 28. The collection optical system 140a is configured to be afocal, and thus able to collect radiation from an infinite cone in front of the probe. The excitation 28 and collection 38 beams overlap over a large patch 102 on the surface of the sample 100. This embodiment is particularly useful for samples which can only be exposed to low intensity excitation light to avoid damage, such as live tissues and fragile chemical compounds.

The typical detectors available currently have heights of roughly 3, 6, 12 and 25 mm, for example. Typical diameters for the optics in the delivery optical system would be 125, 250, 500, 1000, 1800, 2500 microns, and any amount therebetween. The corresponding hole diameters in the first lens of the collection optical system would be approximately 250, 350, 700, 1250, 2100, 3000 microns, and any amount therebetween. Typical core/cladding diameters for the excitation fibers would be 25/125, 50/125, 100/120, 200/240, 300/330, 400/440 for multimode fibers. Typical core/cladding diameters for the collection fibers would be 25/30, 35/42, 50/60, 100/110, 200/220, 300/330, 400/440 and 600/660. Typical numerical apertures for both collection and excitation fibers would be 0.06, 0.10-0.12, 0.16, 0.22, 0.26-0.28, 0.34, 0.37-0.39, 0.48, 0.53 and any amount therebetween. Typical diameters of the optical components in the collection optical system would be 0.8, 1.0, 1.5, 2.0, 3.0, 5.0, 10.0, 12.7, 20, 25, 38, 50 mm, and any amount therebewteen.

It will be clear to those skilled in the relevant arts that the embodiments illustrated in FIG. 13A-D are just some of the possible probe configurations. Other embodiments, suited to particular measurement requirements can be generated based on the principles described in this disclosure without exceeding its scope.

The present invention also provides an spectroscopic measurement system comprising, a fiber optic probe assembly comprising, a housing for containing a first optical system and a second optical system, a delivery light guide comprising one or more than one delivery optical fiber for transmitting excitation radiation from a radiation source disposed at a proximal end of the light guide to the first optical system, the first optical system comprising one or more than one first optical element, the one or more than one first optical element for forming a substantially collimated illumination beam from the excitation radiation, an optically opaque tubular sleeve fitted over the first optical system to optically isolate the first optical system and the delivery light guide from the second optical system so that the excitation radiation transmitted by the delivery light guide exits through an exit face of the first optical system, the second optical system comprising one or more than one second optical element for gathering optical radiation scattered from a sample and forming the optical radiation into a collection beam, a collection light guide comprising one or more than one collection optical fiber for accepting the collection beam and transmitting the collection beam to an analyzer;

the radiation source in optical communication with a proximal end of the delivery light guide, the analyzer comprising a spectrograph with an entrance aperture and a radiation detector, the entrance aperture disposed in an object plane of the spectrograph and coupled to the proximal end of the collection light guide, the radiation detector disposed in an image plane of the spectrograph.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. Fiber optic probe assembly comprising,
   a housing for containing a first optical system and a second optical system,
   a delivery light guide comprising one or more than one delivery optical fiber for transmitting excitation radiation from a radiation source disposed at a proximal end of the light guide to the first optical system disposed at a distal end of the light guide, the first optical system comprising one or more than one first optical element, the one or more than one first optical element for forming a substantially collimated illumination beam from the excitation radiation,
   an optically opaque tubular sleeve fitted over the first optical system to optically isolate the first optical system and the delivery light guide from the second optical system so that the excitation radiation transmitted by the delivery light guide exits through an exit face of the first optical system,
   the second optical system comprising one or more than one second optical element for gathering optical radiation scattered from a sample and forming the optical radiation into a collection beam, the one or more than one second optical element comprising a collimating optical element for collimating the collection beam to produce a collimated collection beam, and a focusing optical element, for focusing the collimated collection beam to produce a focused collection beam, and coupling the focused collection beam into a collection light guide, the collection light guide comprising one or more than one collection optical fiber for accepting the focused collection beam and transmitting the focused collection beam to an analyzer,
   the first and second optical systems are disposed within the housing so that an emission cone of the first optical system and an acceptance cone of the second optical system substantially overlap.

2. The fiber optic probe assembly of claim 1, wherein the one or more second optical element further comprises one or more than one filter element positioned between the collimating optical element and the focusing optical element.

3. The fiber optic probe assembly of claim 1, wherein the optically opaque tubular sleeve directs and supports the delivery light guide from a central axis of the first optical system to the outside periphery of the second optical system.

4. The fiber optic probe assembly of claim 1, wherein the one or more than one first optical element comprises a collimating optical element for collimating the excitation radiation to produce the collimated illumination beam and a focusing optical element, for focusing the collimated illumination beam.

5. The fiber optic probe assembly of claim 4, wherein the one or more than one first optical element further comprises one or more than one filter element positioned between the collimating optical element and the focusing optical element.

6. The fiber optic probe assembly of claim 1, wherein the one or more than one first optic element of the first optical system is selected from a refractive optical lens, and a gradient index optical lens.

7. The fiber optic probe assembly of claim 1, further comprising an optically transparent window element disposed at a sample face of the second optical system, the window element receives the optical radiation scattered by the sample, and isolates the fiber optic probe from the sample.

8. The fiber optic probe assembly of claim 1, wherein said delivery light guide is comprised of a single mode optical fiber with a cutoff wavelength appropriate for the excitation radiation employed.

9. The fiber optic probe assembly of claim 1, wherein the delivery light guide, the collection light guide, or both the delivery light guide and the collection light guide is comprised of a multi mode optical fiber.

10. The fiber optic probe assembly of claim 1, wherein the collection light guide is comprised of a plurality of multi mode optical fibers disposed in a parallel bundle.

11. The fiber optic probe assembly of claim 1, further comprising a rigid termination at a proximal end of the collection light guide, whereby individual optical fibers of the collection light guide are disposed in a side by side linear array for coupling into the analyzer.

12. A spectroscopic measurement system comprising, the fiber optic probe assembly of claim 1, the radiation source in optical communication with a proximal end of the delivery light guide, the analyzer comprising a spectrograph with an entrance aperture and a radiation detector, the entrance aperture disposed in an object plane of the spectrograph and coupled to the proximal end of the collection light guide, the radiation detector disposed in an image plane of the spectrograph.

13. The spectroscopic measurement system of claim 12, wherein the entrance aperture is rectangular and elongated in one dimension.

14. The spectroscopic measurement system of claim 12, wherein the collection light guide is comprised of a plurality of like optical fibers, disposed in a closely hexagonally packed circular bundle at a distal end of the collection light guide, and in a closely packed linear array at the proximal end of the collection light guide.

15. The spectroscopic measurement system of claim 12, further comprising an optically transparent window positioned at a sample face of the fiber optic probe assembly.

16. The spectroscopic measurement system of claim 12, wherein an input numerical aperture of the second optical system is selected to produce substantial overlap of an illumination volume produced by the collimated illumination beam of the first optical system, and a collection volume of the second optical system, suitable for measurements from weakly scattering samples.

* * * * *